(12) United States Patent
Hirai et al.

(10) Patent No.: US 6,548,511 B1
(45) Date of Patent: Apr. 15, 2003

(54) INSECTICIDAL/ACARICIDAL AGENTS

(75) Inventors: Kenji Hirai, Kanagawa (JP); Takeshi Yoshizawa, Kanagawa (JP); Sachiko Itoh, Tokyo (JP); Natsuko Okano, Kanagawa (JP); Yuriko Nagata, Kanagawa (JP); Chikako Ota, Kanagawa (JP); Toshiki Fukuchi, Kanagawa (JP); Keiko Yoshiya, Kanagawa (JP)

(73) Assignees: Sagami Chemical Research Center, Sagamihara (JP); Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/423,616

(22) PCT Filed: May 14, 1998

(86) PCT No.: PCT/JP98/02123
§ 371 (c)(1),
(2), (4) Date: Feb. 9, 2000

(87) PCT Pub. No.: WO98/51152
PCT Pub. Date: Nov. 19, 1998

(30) Foreign Application Priority Data

May 15, 1997 (JP) .............................. 9-125294

(51) Int. Cl.$^7$ ..................... C07D 239/47; A01N 43/54
(52) U.S. Cl. ....................................... 514/272; 544/321
(58) Field of Search .......................... 544/321; 514/272

(56) References Cited

U.S. PATENT DOCUMENTS

| | | | |
|---|---|---|---|
| 3,980,781 A | 9/1976 | Stewart et al. | 424/251 |
| 5,075,316 A | * 12/1991 | Hubele | 514/275 |
| 5,518,994 A | * 5/1996 | Kawamura et al. | 504/242 |

FOREIGN PATENT DOCUMENTS

| | | | |
|---|---|---|---|
| EP | 0 636 615 A1 | | 2/1995 |
| JP | 62-106084 | | 5/1987 |
| JP | 6-157478 | | 6/1994 |
| JP | 6-321913 | * | 11/1994 |
| JP | 7-89941 | | 4/1995 |
| JP | 8-165205 | | 6/1996 |
| JP | 8-188507 | | 7/1996 |

OTHER PUBLICATIONS

Abdel–Fattah et al., "4–Chloro– and 4–hydrazino–pyrimidines as azolopyrimidine precursors", J. Chem. Research (S), 1994, pp. 412–413.

Abdel–Fattah et al., "Reaction with 6–Methyl–2–Thiouracil Synthesis of Dipyrimidino[2,1–b:1',2'–c]Thizine. A New Ring System", Phosphorus, Sulfur, and Silicon, vol. 72, 1992, pp. 145–156.

Gershon, et al., "Some Diazinon Analoques Containing the 4–Trifluoromethyl Group", Monatsh. Chem., 1990, pp. 289–292.

Botta et al., "6–Alkyl– and 5,6–Dialkyl–2–Methoxy–4(3H)–Pyrimidinones in the Transformations of Pyrimidines. Conversion inot 2–Substituted Amino– and 4–Chloro–Pyrimidine–Derivatives", Synthetic Communications, 1985, pp. 27–34.

Sanghavi, et al., "Synthesis and Study of 2–Arylamino–4–(Substituted amino)–6–Methylpyrimidines as Possible Antimalarial Agents. I", Bulletin of Haffkine Institute, vol. 8, No. 3, 1980, pp. 95–101.

Ivashchenko, et al., "Synthesis and study of derivatives of 2,4–diamino– and 2–amino–4–(1H–pyrazol–1–y1)pyrimidine", Khim. Geterotsikl. Soedin., 1980, pp. 404–407.

Reznik, et al., "Synthesis and properties of pyrimidinylalkylphosphonic acids. 11. Reaction of diphenyluracilphosphates with amines", IZV. AKAD. NAUK SSSR, SER. KHIM., 1975, pp. 1604–1608.

Furukawa, et al., "Condensation of arylbiguanides with diketene", Synthesis, 1973, pp. 536–537.

Gehlen, et al., "2–Amino–1,3,4–oxadiazoles. XXXVI. Reaction of 1,3,4–oxadiazolo'3,2–a!pyrimidinones with amines", Arch. PHARM. (Weinheim), 1970, pp. 511–513.

* cited by examiner

*Primary Examiner*—Deepak R. Rao
(74) *Attorney, Agent, or Firm*—Oblon, Spivak, McClelland, Maier & Neustadt, P.C.

(57) ABSTRACT

This invention provides an insecticidal and acaricidal agent which can control various insanitary insects and insects, mites and eggs thereof which are harmful to the agricultural and horticultural products, at a low chemical concentration.

The insecticidal and acaricidal agent of this invention contains an anilinopyrimidinone derivative represented by the following general formula (I)

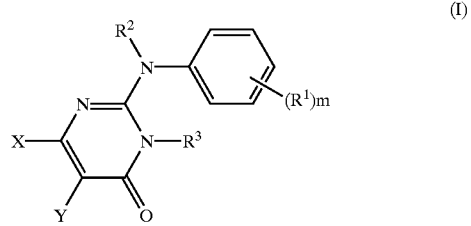

as an active ingredient.

18 Claims, No Drawings

INSECTICIDAL/ACARICIDAL AGENTS

This application is a 371 of PCT/JP98/02123 filed May 14, 1998.

DESCRIPTION

1. Technical Field

This invention relates to an insecticidal and acaricidal agent which contains an anilinopyrimidinone derivative as an active ingredient. Particularly, it relates to an insecticidal and acaricidal agent which is effective for controlling insect pests of agricultural and horticultural products.

2. Background Art

In the field of agriculture and horticulture, various insecticides have been developed and put into practical use for the purpose of controlling various types of disease and insect damage. However, the generally used insecticides for agricultural and horticultural use are not always satisfactory in terms of their insecticidal effect, insecticidal spectrum or residual effect. Also, it cannot be said that they satisfy certain requirements such as reduction of the number of times of application and of the amount of a chemical to be applied.

In addition, there is a problem regarding the generation of disease and insect pests which acquired resistance to generally used agricultural chemicals. For example, in the case of the cultivation of crops such as vegetables, fruit trees, flowers and ornamental plants, tea plants, wheat and related crops and rice plants, various disease and insect pests which acquired resistance to various types of agricultural chemicals such as of triazole, imidazole, pyrimidine, benzimidazole, dicarboxyimide, phenylamide and organic phosphate systems have been found in various districts, and difficulty in preventing these disease and insect pests has been increasing every year.

Though there are certain agricultural chemicals which are not possessed of the resistance to disease and insect pests yet (e.g., dithiocarbamate and phthalimide agricultural chemicals), these chemicals are not desirable from the viewpoint, for example, of environmental pollution because of their generally large amount to be applied and application times. In consequence, great concern has been directed toward the development of a novel insecticide which can show sufficient preventive activity with a low applying amount upon various disease and insect pests which acquired resistance to the general agricultural and horticultural insecticides and also has less bad influence upon the natural environment. Regarding the acaricides, great concern has also been directed toward the development of an acaricide which shows excellent preventive activity upon mites having resistance to generally used acaricides and has high safety.

2-Arylaminopyrimidinone derivatives having herbicidal activities and plant growth regulator actions have been disclosed in WO 93/21162 (an unexamined published Japanese patent application No. 6-321913). However, the just described document does not describe about physiological activities of these compounds other than their herbicidal activities and plant growth regulator actions, such as insecticidal and acaricidal activities.

DISCLOSURE OF THE INVENTION

The inventors of the present invention have conducted intensive studies searching for an insecticidal and acaricidal agent which shows high preventive activity upon various disease and insect pests having resistance to the conventional insecticides and acaricides for agricultural and horticultural use and also has high safety with alleviated problems such as residual toxicity and environmental pollution, and have found as a result of the efforts that an anilinopyrimidinone derivative having a specified structure is a compound having the aforementioned characteristics, thus resulting in the accomplishment of the present invention.

Accordingly, the present invention relates to an insecticidal and acaricidal agent which contains, as an active ingredient, an anilinopyrimidinone derivative represented by a general formula (I)

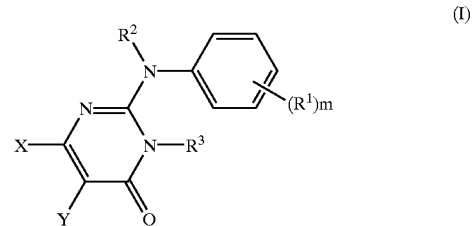

(I)

(wherein $R^1$ represents a hydrogen atom, a halogen atom, a $C_1$–$C_4$ alkyl group, a $C_1$–$C_4$ alkoxy group, a ($C_1$–$C_4$ alkoxy) $C_1$–$C_4$ alkyl group, a $C_1$–$C_4$ haloalkyl group, a $C_1$–$C_4$ haloalkoxy group, a $C_1$–$C_4$ alkylthio group, a $C_1$–$C_4$ alkylsulfinyl group, a $C_1$–$C_4$ alkylsulfonyl group, a $C_1$–$C_5$ acyl group, a ($C_1$–$C_4$ alkoxy)carbonyl group, a $C_3$–$C_6$ alkenyl group, a $C_3$–$C_6$ alkenyloxy group, a $C_3$–$C_6$ alkynyl group, a $C_3$–$C_6$ alkynyloxy group, a $C_1$–$C_5$ acyloxy group, a ($C_1$–$C_4$ alkoxy)$C_1$–$C_4$ alkoxy group, a carboxy($C_1$–$C_4$ alkyl) group, a ($C_1$–$C_4$ alkoxy)carbonyl($C_1$–$C_4$ alkyl) group, a carboxy ($C_1$–$C_4$ alkoxy) group, a ($C_1$–$C_4$ alkoxy)carbonyl($C_1$–$C_4$ alkoxy) group, a $C_1$–$C_4$ alkylamino group, a di($C_1$–$C_4$ alkyl)amino group, a $C_1$–$C_5$ acylamino group, a $C_1$–$C_4$ alkylsulfonylamino group, a mercapto group, a cyano group, a carboxy group, an amino group or a hydroxyl group, m is an integer of from 1 to 5, with the proviso that $R^1$ may be the same or different from each other when m is an integer of from 2 to 5, $R^2$ represents a hydrogen atom, a $C_1$–$C_6$ alkyl group, a $C_2$–$C_6$ alkenyl group, a $C_3$–$C_6$ alkynyl group, a $C_1$–$C_6$ haloalkyl group, a ($C_1$–$C_4$ alkoxy)$C_1$–$C_4$ alkyl group, a $C_1$–$C_4$ alkoxy($C_1$–$C_4$ alkoxy)$C_1$–$C_4$ alkyl group, a ($C_1$–$C_4$ haloalkoxy)$C_1$–$C_4$ alkyl group, a ($C_1$–$C_4$ alkylthio)$C_1$–$C_4$ alkyl group, a carboxy($C_1$–$C_4$ alkyl) group, a ($C_1$–$C_4$ alkoxy)carbonyl($C_1$–$C_4$ alkyl) group, a ($C_1$–$C_4$ alkoxy)carbonyloxy($C_1$–$C_4$ alkyl) group, a ($C_1$–$C_5$ acyloxy)$C_1$–$C_4$ alkyl group, a cyano($C_1$–$C_4$ alkyl) group, a cyanothio ($C_1$–$C_4$ alkyl) group, a $C_1$–$C_5$ acyl group, a ($C_1$–$C_4$ alkoxy) carbonyl group, an aminocarbonyl group, a ($C_1$–$C_6$ alkyl) aminocarbonyl group, a di($C_1$–$C_6$ alkyl)aminocarbonyl group, a ($C_1$–$C_6$ alkyl)sulfonyl group, a benzenesulfonyl group which may be substituted or a $C_7$–$C_8$ aralkyl group which may be substituted, $R^3$ represents a hydrogen atom, a $C_1$–$C_6$ alkyl group, a $C_3$–$C_6$ alkenyl group, a $C_3$–$C_6$ alkynyl group, a $C_3$–$C_7$ cycloalkyl group or an amino group, X represents a halogen atom, a $C_1$–$C_4$ alkyl group or a $C_1$–$C_4$ haloalkyl group, and Y represents a hydrogen atom or a halogen atom).

BEST MODE OF CARRYING OUT THE INVENTION

In the anilinopyrimidinone derivative represented by the general formula (I) as the active ingredient of the insecticidal and acaricidal agent of the present invention, illustrative examples of $R^1$ include hydrogen atom, fluorine atom, chlorine atom, bromine atom and iodine atom; alkyl groups such as methyl, ethyl, propyl, isopropyl, butyl, isobutyl, sec-butyl and tert-butyl; alkoxy groups such as methoxy, ethoxy, propoxy, isopropoxy, butoxy, isobutoxy, sec-butoxy and tert-butoxy; alkoxyalkyl groups such as methoxymethyl, 2-methoxyethyl, ethoxymethyl and 2-ethoxyethyl; haloalkyl groups such as fluoromethyl, chloromethyl, bromomethyl, trichloromethyl, trifluoromethyl, 1-chloroethyl, 2-chloroethyl and 3-chloropropyl; haloalkoxy groups such as trifluoromethoxy, difluoromethoxy, 2-chloroethoxy, 3-chloropropoxy, 2-chloro-1-methylethoxy and 2,2,2-trifluoroethoxy; alkylthio groups such as methylthio, ethylthio, propylthio, isopropylthio, butylthio, isobutylthio, sec-butylthio and tert-butylthio; alkylsulfinyl groups such as methylsulfinyl, ethylsulfinyl, propylsulfinyl, isopropylsulfinyl, butylsulfinyl, isobutylsulfinyl, sec-butylsulfinyl and tert-butylsulfinyl; alkylsulfonyl groups such as methylsulfonyl, ethylsulfonyl, propylsulfonyl, isopropylsulfonyl, butylsulfonyl, isobutylsulfonyl, sec-butylsulfonyl and tert-butylsulfonyl; acyl groups such as formyl, acetyl, propionyl, butyryl, valeryl and pivaloyl; alkoxycarbonyl groups such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl; alkenyl groups such as 2-propenyl and 3-methyl-2-propenyl; alkenyloxy groups such as 2-propenyloxy and 2-butenyloxy; alkynyl groups such as propargyl, 2-butinyl and 1-butin-3-yl; alkynyloxy groups such as 2-propynyloxy and 1-methyl-2-propynyloxy; acyloxy groups such as acetoxy and propionyloxy; alkoxyalkoxy groups such as methoxymethoxy, ethoxymethoxy, isopropoxymethoxy and 2-methoxyethoxy; carboxyalkyl groups such as carboxymethyl and 1-(carboxy)ethyl; alkoxycarbonylalkyl groups such as methoxycarbonylmethyl, ethoxycarbonylmethyl and 1-(methoxycarbonyl)ethyl; carboxyalkoxy groups such as carboxymethoxy and 1-(carboxy)ethoxy; alkoxycarbonylalkoxy groups such as methoxycarbonylmethoxy, ethoxycarbonylmethoxy and 1-(methoxycarbonyl)ethoxy; alkylamino groups such as methylamino, ethylamino, propylamino, isopropylamino and butylamino; dialkylamino groups such as dimethylamino, diethylamino and methylpropylamino; acylamino groups such as acetylamino and propionylamino; alkylsulfonylamino groups such as methylsulfonylamino and ethylsulfonylamino; mercapto group; cyano group; carboxy group; amino group; and hydroxyl group.

Illustrative examples of $R^2$ in the general formula (I) include hydrogen atom; alkyl groups such as methyl, ethyl, propyl, isopropyl, butyl, isobutyl, sec-butyl, tert-butyl, pentyl and hexyl; alkenyl groups such as 2-propenyl and 2-butenyl; alkynyl groups such as propargyl, 1-butin-3-yl and 2-butinyl; haloalkyl groups such as chloromethyl, trichloromethyl, 2-chloroethyl and 3-fluoropropyl; alkoxyalkyl groups such as methoxymethyl, ethoxymethyl, propyloxymethyl, butyloxymethyl, 1-methoxyethyl and 2-methoxyethyl; alkoxyalkoxyalkyl groups such as 2-methoxyethoxymethyl and 2-ethoxyethoxymethyl; haloalkoxyalkyl groups such as trichloromethoxymethyl and trifluoromethoxymethyl; alkylthioalkyl groups such as methylthiomethyl, ethylthiomethyl, 1-(methylthio)ethyl and 2-(methylthio)ethyl; carboxyalkyl groups such as carboxymethyl, 1-(carboxy)ethyl and 2-(carboxy)ethyl; alkoxycarbonylalkyl groups such as methoxycarbonylmethyl, ethoxycarbonylmethyl, propyloxycarbonylmethyl, isopropyloxycarbonylmethyl, 1-(methoxycarbonyl)ethyl, 2-(methoxycarbonyl)ethyl and 1-(methoxycarbonyl)propyl; alkoxycarbonyloxyalkyl groups such as methoxycarbonyloxymethyl, ethoxycarbonyloxymethyl, isopropyloxycarbonyloxymethyl and 1-(methoxycarbonyloxy)ethyl; acyloxyalkyl groups such as formyloxymethyl, acetyloxymethyl, propionyloxymethyl, butyryloxymethyl and pivaloyloxymethyl; cyanoalkyl groups such as cyanomethyl and 1-cyanoethyl; cyanothioalkyl groups such as cyanothiomethyl; acyl groups such as formyl, acetyl, propionyl, butyryl, valeryl and pivaloyl; alkoxycarbonyl groups such as methoxycarbonyl, ethoxycarbonyl, propyloxycarbonyl, isopropoxycarbonyl, butoxycarbonyl, isobutoxycarbonyl and tert-butoxycarbonyl; carbamoyl group; alkylaminocarbonyl groups such as methylcarbamoyl, ethylcarbamoyl and cyclohexylcarbamoyl; dialkylaminocarbonyl groups such as dimethylcarbamoyl, diethylcarbamoyl, ethylpropylcarbamoyl, cyclohexylethylcarbamoyl, 1-pyrrolidinylcarbonyl, piperidinocarbonyl and morpholinocarbonyl; alkylsulfonyl groups such as methylsulfonyl, ethylsulfonyl, isopropylsulfonyl, butylsulfonyl and isobutylsulfonyl; benzenesulfonyl groups which may be substituted, such as benzenesulfonyl and p-toluenesulfonyl; and aralkyl groups which may be substituted, such as benzyl, 4-chlorobenzyl, 4-fluorobenzyl, 4-methylbenzyl, 4-trifluoromethylbenzyl, 4-methoxybenzyl, α-phenethyl and β-phenethyl.

Illustrative examples of $R^3$ in the general formula (I) include hydrogen atom; alkyl groups such as methyl, ethyl, propyl, isopropyl, butyl, isobutyl, sec-butyl, tert-butyl, pentyl, neopentyl and hexyl; alkenyl groups such as 2-propenyl and 2-butenyl; alkynyl groups such as propargyl, 2-butinyl and 1-butin-3-yl; cycloalkyl groups such as cyclopropyl, cyclobutyl, cyclopentyl and cyclohexyl; and amino group.

Illustrative examples of X in the general formula (I) include halogen atoms such as fluorine atom, chlorine atom, bromine atom and iodine atom; alkyl groups such as methyl, ethyl, propyl, isopropyl, butyl, isobutyl, sec-butyl and tert-butyl; and haloalkyl groups such as trichloromethyl, trifluoromethyl and 2,2,2-trifluoroethyl; and examples of Y include hydrogen atom, fluorine atom, chlorine atom, bromine atom and iodine atom.

Among anilinopyrimidinone derivatives represented by the general formula (I), a preferred compound from the viewpoint of insecticidal and acaricidal activities is an anilinopyrimidinone derivative in which $R^1$ is a halogen atom or a haloalkyl group, $R^2$ is hydrogen atom, an alkyl group, an alkoxyalkyl group, an alkylthioalkyl group, an acyloxyalkyl group, an alkoxycarbonyl group or an alkylsulfonyl group, $R^3$ is an alkyl group, an alkenyl group or a cycloalkyl group, X is a halogen atom or a haloalkyl group, Y is hydrogen atom or a halogen atom and m is from 1 to 3. Particularly, among anilinopyrimidinone derivatives in which X is trifluoromethyl group, an anilinopyrimidinone derivative in which $R^1$ is chlorine atom or trifluoromethyl group, m is 2 or 3 and Y is hydrogen atom or chlorine atom is preferred in view of its strong insecticidal and acaricidal activities.

Though most of the anilinopyrimidinone derivatives represented by the general formula (I) are compounds which are included in the general formula described in WO 93/21162, the specification of this WO 93/21162 does not describe insecticidal activity and acaricidal activity of these compounds. In addition, WO 93/21162 discloses a general formula which includes a markedly broad range of compounds, but only a part of these compound are actually synthesized and checked for their herbicidal or plant growth regulating activity.

Among the anilinopyrimidinone derivatives of the present invention having excellent effect as an insecticidal and acaricidal agent, an anilinopyrimidinone derivative represented by the following general formula (II)

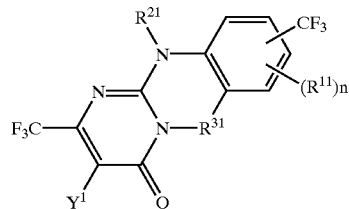

(II)

(wherein $R^{11}$ represents chlorine atom or trifluoromethyl group, n is 1 or 2, wherein $R^{11}$ may be the same or different from each other when n is 2, $R^{21}$ represents a hydrogen atom, a $C_1$–$C_6$ alkyl group, a $C_2$–$C_6$ alkenyl group, a $C_3$–$C_6$ alkynyl group, a $C_1$–$C_6$ haloalkyl group, a ($C_1$–$C_4$ alkoxy)$C_1$–$C_4$ alkyl group, a $C_1$–$C_4$ alkoxy($C_1$–$C_4$ alkoxy)$C_1$–$C_4$ alkyl group, a ($C_1$–$C_4$ haloalkoxy)$C_1$–$C_4$ alkyl group, a ($C_1$–$C_4$ alkylthio)$C_1$–$C_4$ alkyl group, a carboxy($C_1$–$C_4$ alkyl) group, a ($C_1$–$C_4$ alkoxy)carbonyl($C_1$–$C_4$ alkyl) group, a ($C_1$–$C_4$ alkoxy)carbonyloxy($C_1$–$C_4$ alkyl) group, a ($C_1$–$C_5$ acyloxy)$C_1$–$C_4$ alkyl group, a cyano($C_1$–$C_4$ alkyl) group, a cyanothio($C_1$–$C_4$ alkyl) group, a $C_1$–$C_5$ acyl group, a ($C_1$–$C_4$ alkoxy)carbonyl group, an aminocarbonyl group, a ($C_1$–$C_6$ alkyl)aminocarbonyl group, a di($C_1$–$C_6$ alkyl) aminocarbonyl group, a ($C_1$–$C_6$ alkyl)sulfonyl group, a benzenesulfonyl group which may be substituted or a $C_7$–$C_8$ aralkyl group which may be substituted, $R^{31}$ represents a $C_1$–$C_6$ alkyl group, a $C_3$–$C_6$ alkenyl group or a $C_3$–$C_7$ cycloalkyl group, and $Y^1$ represents a hydrogen atom or a halogen atom) is a novel compound which is not illustratively shown in WO 93/21162.

Production method of the anilinopyrimidinone derivative of general formula (I) is not particularly limited, and it can be produced, for example, by the following production methods.

[Production method 1]

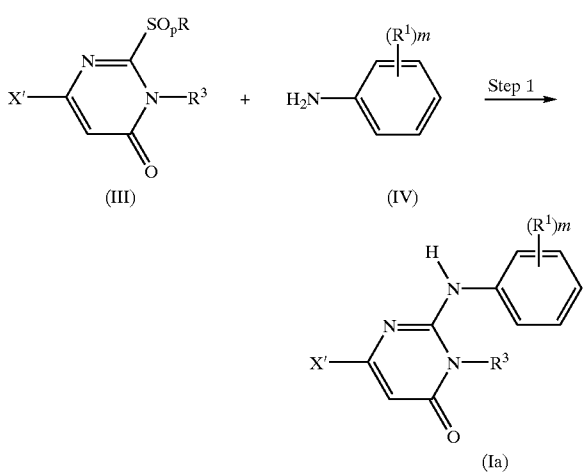

(In the above reaction formula, R is a $C_1$–$C_6$ alkyl group, p is 0 or 2, X' is a $C_1$–$C_4$ alkyl group or a $C_1$–$C_4$ haloalkyl group, and $R^1$, $R^3$ and m are as defined in the foregoing.)

[Production method 2]

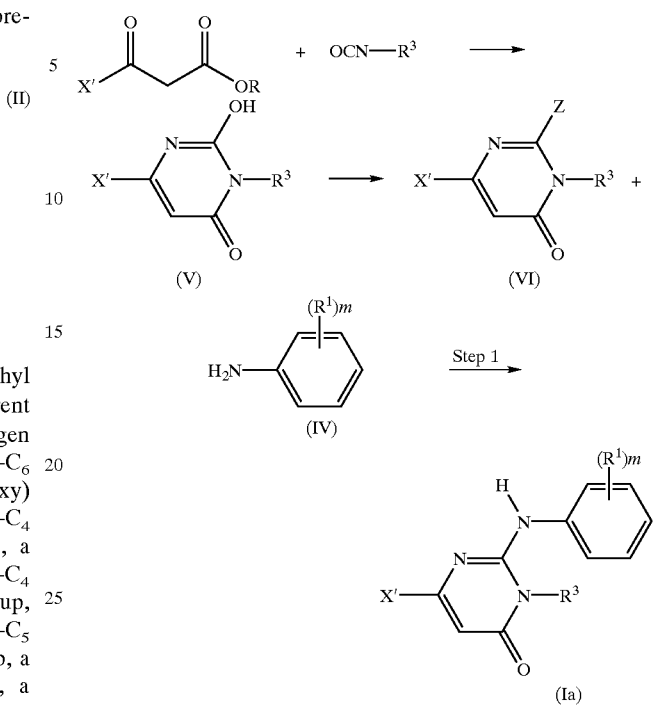

(In the above reaction formula, R is a $C_1$–$C_6$ alkyl group, Z is a halogen atom, X' is a $C_1$–$C_4$ alkyl group or a $C_1$–$C_4$ haloalkyl group, and $R^1$, $R^3$ and m are as defined in the foregoing.)

In the step 1 of the production methods 1 and 2, a compound in which X of the anilinopyrimidinone derivative (I) is a $C_1$–$C_4$ alkyl group or a $C_1$–$C_4$ haloalkyl group, namely the anilinopyrimidinone derivative (Ia), is produced by using a 2-alkylthiopyrimidinone or 2-alkylsulfonylpyrimidinone derivative (III) or a 2-halogenopyrimidinone derivative (VI) as a starting material and allowing the material to react with anilines (IV).

It is desirable to carry out the reaction of step 1 in the presence of a base, in view of high yield. Illustrative examples of the base include alkali metal bases such as sodium hydride, potassium hydride, lithium amide, sodium amide, lithium diisopropylamide, butyl lithium, tert-butyl lithium, trimethysilyl lithium, lithium hexamethyldisilazide, sodium carbonate, potassium carbonate, sodium acetate, potassium acetate, sodium methoxide, sodium ethoxide and potassium tert-butoxide, and organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane and imidazole. The compound of interest can be obtained with a high yield when the base is used in an amount of from 0.1 to 2.0 equivalents based on the substrate.

This reaction can be carried out in a solvent, and any solvent which does not spoil the reaction can be used. Examples of the reaction-inert solvent include amide solvents such as N,N-dimethylformamide (DMF), N,N-dimethylacetamide and N-methylpyrrolidone, nitrile solvents such as acetonitrile and propionitrile, aromatic hydrocarbon solvents such as benzene, toluene, xylene and chlorobenzene, aliphatic hydrocarbon solvents such as pentane, hexane and octane, ether solvents such as diethyl ether, diisopropyl ether, tetrahydrofuran (THF), dimethoxyethane (DME) and 1,4-dioxane, and dimethylsulfoxide (DMSO), or mixed solvents thereof.

The compound of interest can be obtained with a high yield by carrying the reaction at a temperature optionally selected within the range of from −78 to 100° C.

In the production method 1, the 2-alkylthiopyrimidinone derivative to be used as the starting material can be produced easily by carrying out cyclization condensation reaction of a 3-aminoacrylic acid ester derivative with isothiocyanates in accordance with a known method (e.g., WO 93/21162). Also, the 2-alkylsulfonylpyrimidinone derivative can be produced by oxidizing the 2-alkylthiopyrimidinone derivative. In addition, the 2-halogenopyrimidinone derivative (VI) to be used as the starting material in the production method 2 can be produced easily by carrying out chlorination of the 2-hydroxypyrimidinone derivative (V) which can be produced easily by the cyclization condensation reaction of a β-keto ester derivative with isocyanates, using a halogenation agent such as phosphorus pentachloride, phosphorus oxytrichloride, phosphorus pentabromide or phosphorus oxytribromide.

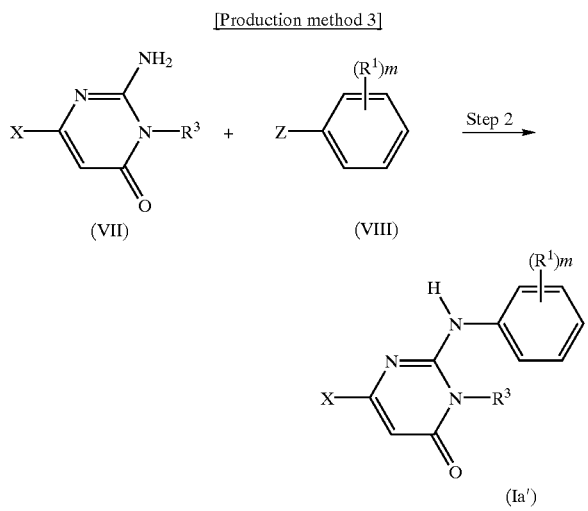

(In the above reaction formula, Z is a halogen atom, and $R^1$, $R^3$, X and m are as defined in the foregoing.)

In the step 2 of production method 3, the anilinopyrimidinone derivative (Ia') is produced by allowing a 2-aminopyrimidinone derivative (VII) to react with a halobenzene derivative (VIII) having an activated halogen atom, in the presence of a base.

It is desirable to carry out the reaction in the presence of a base in view of high yield. Examples of the base include organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane and imidazole, and alkali metal bases such as sodium carbonate, potassium carbonate, sodium bicarbonate, potassium bicarbonate, sodium acetate, potassium acetate, sodium methoxide, sodium ethoxide, potassium tert-butoxide, sodium hydride, potassium hydride, sodium amide, butyl lithium, tert-butyl lithium, lithium diisopropylamide, trimethylsilyl lithium and lithium hexamethyldisilazide. The compound of interest can be obtained with a high yield when the base is used in an amount of from 1 to 1.5 equivalents based on the substrate.

It is desirable to carry out this reaction in a solvent. As the solvent, any solvent which does not spoil the reaction can be used, and its examples include aromatic hydrocarbon solvents such as benzene, toluene, xylene and chlorobenzene, aliphatic hydrocarbon solvents such as pentane, hexane and octane, ether solvents such as diethyl ether, diisopropyl ether, THF, DME and 1,4-dioxane, ketones such as acetone, methyl ethyl ketone and cyclohexanone, halogenated solvents such as chloroform and dichloromethane, nitrile solvents such as acetonitrile and propionitrile, ester solvents such as ethyl acetate, propyl acetate, butyl acetate and methyl propionate, amide solvents such as DMF, N,N-dimethylacetamide and N-methylpyrrolidone, and DMSO, or mixed solvents thereof.

Though it varies depending on the base used and reaction conditions, this reaction can be carried out at a temperature optionally selected within the range of from 0° C. to reflux temperature of the solvent used.

Some of the 2-aminopyrimidinone derivatives (VII) to be used in this step are on the market and easily available, but can also be produced easily by allowing an α-keto ester derivative to react with substituted or unsubstituted guanidine. Also, the halobenzene derivative (VIII) is on the market and easily available. In addition, in the halobenzene derivative (VIII) to be used in this reaction, the halogen atom represented by Z is preferably fluorine atom or bromine atom in view of high reaction yield, and the substituent $R^1$ on the phenyl ring is preferably an electron-withdrawing group such as a halogen atom, trichloromethyl group, trifluoromethyl group or a cyano group, which can activate the halogen atom more effectively.

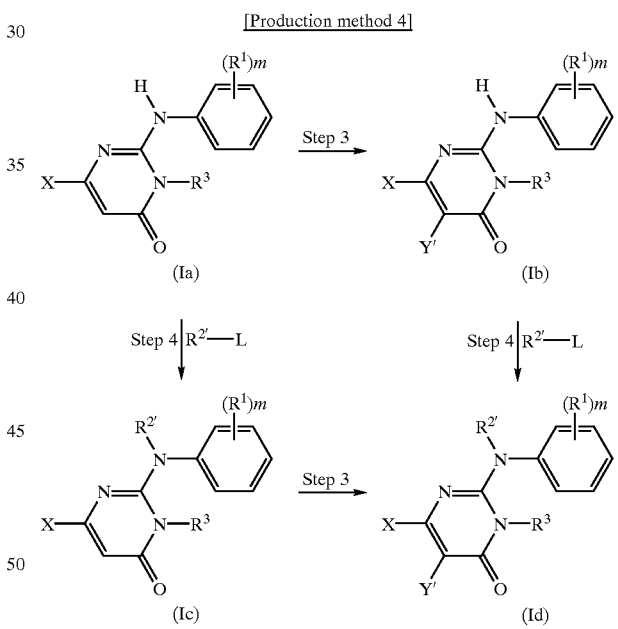

(In the above reaction formula, Y' is a halogen atom, $R^{2'}$ is any one of the substituents represented by $R^2$, excluding hydrogen atom, L is a leaving group, and $R^1$, $R^3$, X and m are as defined in the foregoing.)

In the production method 4, anilinopyrimidinone derivatives (Ib, Ic and Id) are produced by halogenation (step 3) of the 5-position, and alkylation (step 4) on the nitrogen atom of the anilino group at the 2-position, of the anilinopyrimidinone derivative (Ia) obtained in the production methods 1 to 3.

In the step 3, the 5-position of the pyrimidine ring of the anilinopyrimidinone derivative (Ia) or (Ic) is halogenated to produce the corresponding anilinopyrimidinone derivative (Ib) or (Id).

The halogenation can be carried out using a halogenation agent, and examples of the useful halogenation agent include chlorine, bromine, iodine, potassium fluoride, sulfuryl chloride, N-chlorosuccinimide, N-bromosuccinimide, N-iodosuccinimide, tert-butyl hypochlolite, diethylaminosulfa trifluoride, carbon tetrachloride/triphenylphosphine and carbon tetrabromide/triphenylphosphine.

This reaction can be carried out in a solvent which does not spoil the reaction, and its examples include aromatic hydrocarbon solvents such as chlorobenzene and dichlorobenzene, aliphatic hydrocarbon solvents such as pentane, hexane and octane, ether solvents such as diethyl ether, diiosopropyl ether, THF, DME and 1,4-dioxane, halogenated solvents such as chloroform, methylene chloride and carbon tetrachloride and organic acid solvent such as acetic acid and propionic acid, or mixed solvents thereof.

The compound of interest can be obtained with a high yield by carrying the reaction at a temperature optionally selected within the range of from 0 to 100° C.

In the step 4, the anilinopyrimidinone derivative (Ia) or (Ib) is used as the starting material and allowed to react with a substance represented by a general formula $R^{2'}$-L in the presence of a base to produce the corresponding anilinopyrimidinone derivative (Ic) or (Id).

This reaction is carried out in the presence of a base. Examples of the base include alkali metal bases such as sodium hydride, potassium hydride, lithium amide, sodium amide, lithium diisopropylamide, butyl lithium, tert-butyl lithium, trimethylsilyl lithium, lithium hexamethyldisilazide, sodium carbonate, potassium carbonate, sodium acetate, potassium acetate, sodium methoxide, sodium ethoxide and potassium tert-butoxide, and organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane and imidazole. The compound of interest can be obtained with a high yield when the base is used in an amount of from 1 to 2 equivalents based on the substrate.

This reaction can be carried out in a solvent which does not spoil the reaction. Examples of the solvent include amide solvents such as DMF, N,N-dimethylacetamide and N-methylpyrrolidone, nitrile solvents such as acetonitrile and propionitrile, aromatic hydrocarbon solvents such as benzene, toluene, xylene and chlorobenzene, aliphatic hydrocarbon solvents such as pentane, hexane and octane, ether solvents such as diethyl ether, diisopropyl ether, THF, DME and 1,4-dioxane, and DMSO, or mixed solvents thereof.

The compound of interest can be obtained with a high yield by carrying the reaction at a temperature optionally selected within the range of from 0 to 100° C.

In this reaction, the compound of interest can be obtained with more higher yield by the use of a catalyst, and its examples include polyethers such as 18-crown-6, 15-crown-5 and 12-crown-4 and quaternary ammonium salts such as tetrabutylammonium chloride, tetrabutylammonium bromide, triethylbenzylammonium chloride, tetrabutylammonium sulfate and tetraethylammonium iodide.

Regarding the substance ($R^{2'}$-L) to be used in this step, examples of the substituent represented by $R^{2'}$ are as described in the foregoing, and examples of the leaving group represented by L include halogen atoms such as chlorine atom, bromine atom and iodine atom and substituted sulfonyloxy groups such as methanesulfonyloxy group, benzenesulfonyloxy group and p-toluenesulfonyloxy group. In consequence, illustrative examples of the substance represented by the general formula $R^{2'}$-L include methyl bromide, methyl iodide, ethyl bromide, isopropyl iodide, allyl chloride, allyl bromide, methallyl chloride, allyl methanesulfonate, propargyl bromide, propargyl p-toluenesulfonate, 1-butin-3-yl p-toluenesulfonate, difluorochloromethane, 1-bromo-3-fluoropropane, 3,3,3-trifluoropropyl iodide, chloromethyl methyl ether, chloromethyl ethyl ether, chloromethyl propyl ether, chloromethyl isopropyl ether, chloromethyl butyl ether, chloromethyl isobutyl ether, chloromethyl (methoxyethyl) ether, chloroethyl (chloromethyl) ether, chloromethyl methyl thioether, chloroacetic acid, bromoacetic acid, α-chloropropionic acid, methyl chloroacetate, ethyl chloroacetate, methyl bromoacetate, isopropyl bromoacetate, methyl α-chloropropionate, ethyl α-chloropropionate, ethyl(1-chloroethyl) carbonate, ethyl(1-bromoethyl) carbonate, chloromethyl acetate, (1-chloroethyl) acetate, (bromomethyl) acetate, chloroacetonitrile, α-chloropropionitrile, cynaothiomethyl chloride, cyanothiomethyl bromide, acetyl chloride, acetyl bromide, propionyl chloride, butyryl chloride, valeryl chloride, pivaloyl chloride, methyl chloroformate, ethyl chloroformate, propyl chloroformate, isopropyl chloroformate, isobutyl chloroformate, tert-butyl chloroformate, methylcarbamoyl chloride, ethylcarbamoyl chloride, isopropylcarbamoyl chloride, butylcarbamoyl chloride, sec-butylcarbamoyl chloride, cyclohexylcarbamoyl chloride, dimethylcarbamoyl chloride, diethylcarbamoyl chloride, diisopropylcarbamoyl chloride, methylethylcarbamoyl chloride, ethylpropylcarbamoyl chloride, ethylcyclohexylcarbamoyl chloride, methylsulfonyl chloride, ethylsulfonyl chloride, isopropylsulfonyl chloride, isobutylsulfonyl chloride, phenylsulfonyl chloride, p-toluenesulfonyl chloride, 4-fluorophenylsulfonyl chloride, 4-chlorophenylsulfonyl chloride, benzyl chloride, benzyl bromide, 4-fluorobenzyl chloride, 4-fluorobenzyl bromide, 4-methoxybenzyl chloride, 4-methoxybenzyl bromide, 3,4-dimethoxybenzyl chloride and α-phenethyl chloride. In addition, dialkyl sulfates such as dimethyl sulfate and diethyl sulfate and α,α-dihaloalkanes such as dibromomethane and chlorobromomethane as described below are also included in the substance ($R^{2'}$-L).

In addition to the aforementioned means, the intended anilinopyrimidinone derivative (Ic) or (Id) can be produced in the step 4 by a method exemplified in the following. That is, by using an α,α-dihaloalkane such as dibromomethane or chlorobroanomethane as the substance and allowing it to react with the anilinopyrimidinone derivative (Ia) or (Ib) in the presence of a base such as sodium hydride or sodium amide, the nitrogen atom of 2-anilino group can be 1-bromoalkylated or 1-chloroalkylated. This reaction can be carried out in an ether solvent such as THF or DME at a reaction temperature of approximately from 0 to 50° C. Though these haloalkyl compounds can be isolated if desired, the anilinopyrimidinone derivative (Ic) or (Id) in which the nitrogen atom of 2-anilino group is alkoxyalkylated or alkylthioalkylated can be produced by allowing these compounds in the reaction system, without isolation, to react with an alkali metal alkoxide or thioalkoxide such as sodium methoxide, sodium ethoxide, potassium methoxide, potassium ethoxide, sodium thiomethoxide or sodium thioethoxide. This reaction can be carried out in an ether solvent such as THF or DME at a reaction temperature selected within the range of from room temperature to reflux temperature of the solvent used.

In addition, in the step 4, the anilinopyrimidinone derivative (Ic) or (Id) is which the nitrogen atom of 2-anilino group is alkoxymethylated can be produced by allowing the anilinopyrimidinone derivative (Ia) or (Ib) and a dialkoxymethane such as dimethoxymethane or diethoxymethane to react with Vilsmeier's reagent in an organic solvent and then treating the resulting product with a tertiary amine. This reaction can be carried out in an aromatic hydrocarbon solvent such as benzene, toluene, xylene or chlorobenzene at a reaction temperature selected within the range of from 0 to 100° C. The Vilsmeier's reagent can be prepared from phosphorus oxychloride, thionyl chloride or phosgene and DMF, but it is desirable to use phosphorus oxychloride in view of high yield. Regarding the tertiary amine, amines such as triethylamine, tripropylamine, tributylamine, N-methylmorpholine and N,N-dimethylaniline can be used.

The anilinopyrimidinone derivative represented by the general formula (I) shows high preventive activity at a low chemical concentration upon insanitary insects or insect pests harmful to the agricultural and horticultural products, particularly upon insects and mites. Examples of the insect pests and mites to be controlled include larvae and imagoes of insects belonging to Lepidoptera such as common cutworm, diamondback moth, smaller tea tortrix, grass leaf roller and rice stem borer; belonging to Hemiptera including rice insects such as brown rice planthopper and whitebacked planthopper, leafhoppers such as green rice leafhopper and tea green leafhopper, aphids such as green peach aphid and cotton aphid, whiteflies such as greenhouse whitefly and stink bugs such as a green stink bug; belonging to Coleoptera such as striped flea beetle, cucurbit leaf beetle and adzuki bean weevil; belonging to Diptera such as housefly and common gnat; and belonging to Orthoptera such as a cockroach (*Periplaneta americana*), and eggs and imagoes of mites belonging to Acarina such as two-spotted spider mite, citrus red mite, Japanese citrus rust mite and broad mite. In consequence, the anilinopyrimidinone derivative (I) is useful as an insecticide and an acaricide for agricultural and horticultural use. As a matter of course, the insects and mites to be controlled by the insecticidal and acaricidal agent of the present invention are not limited to the just exemplified cases.

When the anilinopyrimidinone derivative represented by the general formula (I) is used as agricultural and horticultural insecticide and acaricide, it may be used alone but preferably in the form of a composition produced using a general agricultural adjuvant. Though the form of the insecticidal and acaricidal agent of the present invention is not particularly limited, it is desirable to make it into, for example, emulsifiable concentrates, wettable powders, dusts, flowables, fine granules, granules, tablets, oil solutions, propellents or aerosols. One or more members of the anilinopyrimidinone derivative (I) can be formulated as active ingredients.

The agricultural adjuvant to be used for the production of an insecticidal and acaricidal agent can be used for the purpose, for example, of improving and stabilizing the insecticidal and acaricidal effects and improving the dispersibility. For example, a carrier (diluent), a spreader, an emulsifier, a wetting agent, a dispersing agent and a disintegrating agent can be used.

Examples of the liquid carrier include water, aromatic hydrocarbons such as toluene and xylene, alcohols such as methanol, butanol and glycol, ketones such as acetone and cyclohexanone, amides such as dimethylformamide, sulfoxides such as dimethyl sulfoxide, methylnaphthalene, cyclohexane, animal and plant oils and fatty acids. Examples of the solid carrier include clay, kaolin, talc, diatomaceous earth, silica, calcium carbonate, montmorillonite, bentonite, feldspar, quartz, alumina, sawdust, nitrocellulose, starch and gum arabic.

Regarding the emulsifier and dispersing agent, conventional surfactants can be used, which include anionic, cationic, nonionic and amphoteric surfactants, such as sodium higher alcohol sulfate, strearyltrimethylammonium chloride, polyoxyethylene alkylphenyl ether and laurylbetaine. Also useful are spreaders such as polyoxyethylene nonylphenyl ether and polyoxyethylene laurylphenyl ether; wetting agents such as dialkyl sulfosuccinate; adhesive agents such as carboxymethylcellulose and polyvinyl alcohol; and disintegrating agents such as sodium lignin sulfonate and sodium lauryl sulfate.

Amount of the active ingredient in the insecticidal and acaricidal agent for agricultural and horticultural use is selected within the range of from 4.1 to 99.5% and optionally decided depending on various conditions such as formulation types and application methods, and it is desirable to produce the agent in such a manner that is contains the active ingredient in an amount of approximately from 0.5 to 20% by weight and preferably from 1 to 10% by weight in the case of dusts, approximately from 1 to 90% by weight and preferably from 10 to 80% by weight in the case of wettable powder or approximately from 1 to 90% by weight and preferably from 10 to 40% by weight in the case of emulsifiable concentrates.

For example, in the case of the emulsifiable concentrate, a formulated concentrate of the emulsifiable concentrate can be produced by mixing the anilinopyrimidinone derivative (I) with a solvent and an additive (e.g., surfactant), and the formulated concentrate can be applied by diluting it with water to a predetermined concentration when used. In the case of the wettable powder, a formulated concentrate can be produced by mixing the aforementioned compound as the active ingredient with a solid carrier and an additive (e.g., a surfactant), and the thus formulated concentrate can be applied by diluting it with water to a predetermined concentration when used. In the case of the dust, it can be produced by mixing the active ingredient anilinopyrimidinone derivative (I) with a solid carrier and necessary additives and applied as such, and in the case of the granule, it can be produced by mixing the active ingredient anilinopyrimidinone derivative (I) with a solid carrier, a surfactant and necessary additives and making the mixture into granules which can be applied as such. As a matter of course, production methods of the aforementioned formulation types are not limited to those exemplified in the above and can be selected optionally by those skilled in the art depending on the types of the active ingredient, application purpose and other conditions.

In addition to the anilinopyrimidinone derivative represented by the general formula (I) as the active ingredient, the insecticidal and acaricidal agent of the present invention for agricultural and horticultural use may be formulated with other optional active ingredients such as a fungicide, an insecticide, an acaricide, a herbicide, an insect growth controlling agent, a fertilizer and a soil conditioner. Application method of the insecticidal and acaricidal agent of the present invention for agricultural and horticultural use is not particularly limited, and it can be applied by any of the usual methods such as foliar application, submerged application, soil treatment and seed treatment. For example, in the case of the foliar application, a solution containing from 5 to 1,000 ppm, preferably from 10 to 500 ppm, of the active ingredient can be used in an application amount of approximately from 100 to 200 liters based on 10 a. In the case of the submerged application of granules containing from 5 to 15% of the active ingredient, the application amount is generally from 1 to 10 kg based on 10 a. In the case of the soil treatment, a solution containing from 5 to 1,000 ppm of the active ingredient can be used in an application amount of approximately from 1 to 10 liters based on 1 m². In the case of the seed treatment, a solution containing from 10 to 1,000 ppm of the active ingredient can be used in an application amount of approximately from 10 to 100 ml based on 1 kg of the seed weight.

The present invention is described more illustratively in the following with reference to Example and Test Example, but the invention is not restricted by the following Example and Test Examples unless exceeding the gist thereof.

EXAMPLES

Example 1

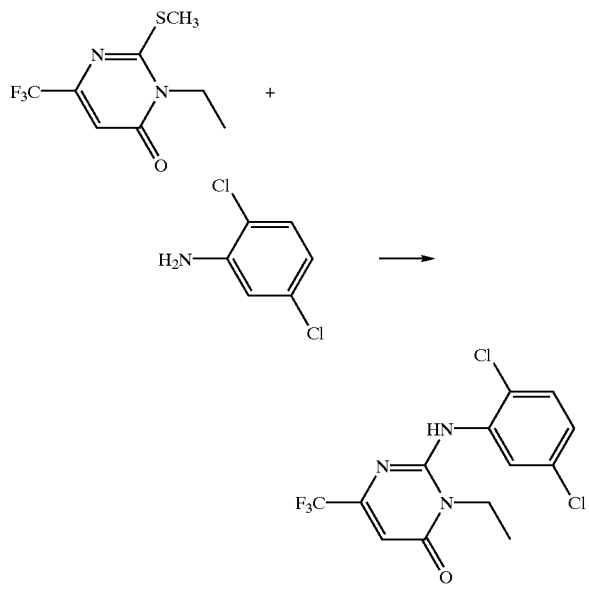

With stirring under ice-cooling, sodium hydride (60% in oil, 3.73 g, 56.0 mmol) and ethyl isothiocyanate (4.38 ml, 56.0 mmol) were added in that order to DMF (35 ml) solution of ethyl 3-amino-4,4,4-trifluorocrotonate, Followed by stirring overnight while gradually returning to room temperature. After completion of the reaction, the reaction solution was concentrated under a reduced pressure, water (20 ml) was added to the thus obtained residue, and then concentrated hydrochloric acid (15 ml) was added. The thus precipitated solid was isolated by filtration, washed with water (100 ml) and then thoroughly dried to obtain 3-ethyl-2-mercapto-6-trifluoromethyl-4-(3H)-pyrimidinone (11.0 g, 99%).

$^1$H-NMR (CDCl$_3$, TMS, ppm): δ 1.32 (38, t, J=7.0 Hz), 4.44 (2H, q, J=7.0 Hz), 6.28 (1H, s), 9.12 (1H, br s).

Next, potassium carbonate (8.15 g, 59.0 mmol) was added to DMF (100 ml) solution of 3-ethyl-2-mercapto-6-trifluoromethyl-4(3H)-pyrimidinone (11.0 g, 49.0 mmol), methyl iodide (3.68 ml, 59.0 mmol) was added with stirring under ice-cooling, followed by stirring for 4 hours while gradually returning to room temperature. After completion of the reaction, the reaction solution was concentrated under a reduced pressure, water (100 ml) and ethyl acetate (100 ml) were added to the thus obtained residue to separate the organic layer, and then the aqueous layer was extracted with ethyl acetate (50 ml×3). The organic layers were combined, washed with water (100 ml×3) and saturated brine (300 ml) and then dried over anhydrous magnesium sulfate. The drying agent was removed by filtration and then the resulting filtrate was concentrated under a reduced pressure to obtain 3-ethyl-2-methylthio-6-trifluoromethyl-4(3H)-pyrimidinone (11.0 g, 94%).

$^1$H-NMR (CDCl$_3$, TMS, ppm): δ 1.35 (3H, t, J=7.0 Hz), 2.61 (3H, s), 4.13 (2H, q, J=7.0 Hz), 6.53 (1H, s).

2,5-Dichloroaniline (0.49 g, 3.0 mmol) was dissolved in DMF (20 ml), and sodium hydride (60% oil, 0.20 g, 5.01 mmol) was added, followed by stirring at room temperature for 20 minutes. Then, 3-ethyl-2-methylthio-6-trifluoromethyl-4(3H)-pyrimidinone (1,14 g, 4.80 mmol) synthesized in the above was added, followed by stirring at 80° C. for 4 hours. After completion of the reaction, ice-water (30 ml) and ethyl acetate (30 ml) were added to the reaction solution to separate the organic layer, and then the aqueous layer was extracted with ethyl acetate (20 ml×3). The organic layers were combined, washed with saturated sodium bicarbonate aqueous solution (50 ml), water (50 ml×2) and saturated brine (80 ml) and then dried over anhydrous magnesium sulfate. The drying agent was removed by filtration and the resulting filtrate was concentrated under a reduced pressure. The thus obtained crude product was purified by a silica gel column chromatography (hexane: ethyl acetate=10:1) and then recrystallized from toluene, thereby obtaining yellow crystals of 2-(2,5-dichlorophenyl)amino-3-ethyl-6-trifluoromethyl-4(3H)-pyrimidinone [Compound No. 6].

Yield: 64%; mp: 167–168° C.; $^1$H-NMR (CDCl$_3$, TMS, ppm): δ 1.50 (3H, t, J=7.56 Hz), 4.23 (2H, q, J=7.56 Hz), 6.43 (1H, s), 7.20–7.48 (3H, m), 8.65 (1H, d, J=2.52 Hz).

Example 2

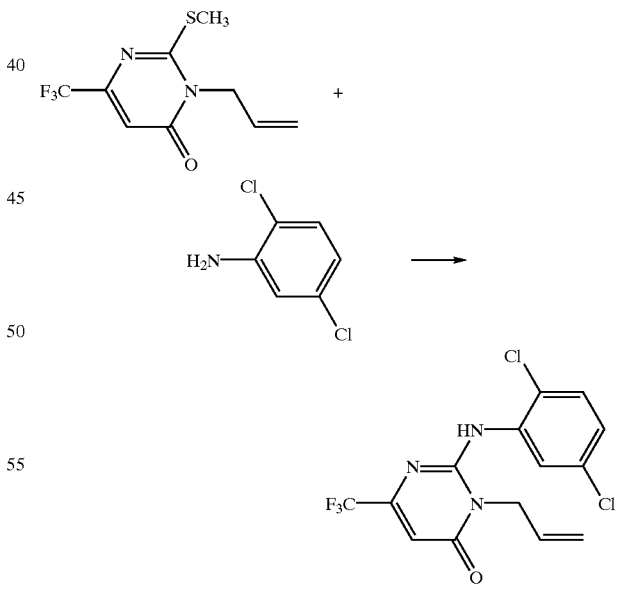

Sodium hydride (60% in oil, 2.71 q, 60.0 mmol) was added to DMF (40 ml) solution of ethyl 3-amino-4,4,4-trifluorocrotonate spending 30 minutes under ice-cooling, followed by stirring for 20 minutes. Next, allyl isothiocyanate (5.3 ml, 54.0 mmol) was added under ice-cooling, followed by overnight stirring while gradually returning to room temperature. After completion of the reaction, the reaction solution was concentrated under a reduced pressure, water (40 ml) and 2 N hydrochloric acid (1.25 ml) were added to the thus obtained residue. The thus precipitated solid was isolated by filtration, washed with water and hexane and then thoroughly dried to obtain light yellow solid of 3-allyl-2-mercapto-6-trifluoromethyl-4(3H)-pyrimidinone (12.7 g, 89%).

$^1$H-NMR (CDCl$_3$, TMS, ppm): δ 4.99 (2H, d, J=5. 8 Hz), 5.27–5.42 (2H, m), 5.86–5.99 (1H, m), 6.31 (1H, s), 9.18 (1H, br s).

Next, potassium carbonate (22.5 g, 163 mmol) and methyl iodide (10.2 ml, 164 mmol) were added to DMF (110 ml) solution of 3-allyl-2-mercapto-6-trifluoromethyl-4(3H)-pyrimidinone (32.1 g, 136 mmol) with stirring under ice-cooling, followed by stirring for 23 hours while gradually returning to room temperature. After completion of the reaction, the reaction solution was concentrated under a reduced pressure, saturated brine (100 ml), water (100 ml) and ethyl acetate (300 ml) were added to the thus obtained residue to separate the organic layer and then the aqueous layer was extracted with ethyl acetate (100 ml×2). The organic layers were combined, washed with saturated brine (50 ml×2) and then dried over anhydrous magnesium sulfate. The drying agent was removed by filtration and the resulting filtrate was concentrated under a reduced pressure. The thus obtained crude product was purified, by a silica gel column chromatography (hexane~hexane:ethyl acetate=9:1) to obtain white solid of 3-allyl-2-methylthio-6-trifluoromethyl-4(3H)-pyrimidinone (26.9 g, 79%).

$^1$H-NMR (CDCl$_3$, TMS, ppm): δ 2.60 (3H, s), 4.69 (2H, d, J=5.7 Hz), 5.25–5.34 (2H, m), 5.76–5.96 (1H, m), 6.55 (1H, s).

The thus obtained 3-allyl-2-methylthio-6-trifluoromethyl-4(3H)-pyrimidinone was allowed to react with 2,5-dichloroaniline in accordance with the method of Example 1 to obtain 3-allyl-2-(2,-dichlorophenylamino)-6-trifluoromethyl-4(3H)-pyrimidinone [Compound No. 7].

Yield: 12%; mp: 118–120° C.; $^1$H-NMR (CDCl$_3$, TMS, ppm): δ 4.84 (2H, ddd, J=5.2, 1.7 and 1.7 Hz), 5.44 (1H, ddt, J=17.4, 1.7 and 1.7 Hz), 5.48 (1H, ddt, J=10.2, 1.7 and 1.7 Hz), 5.95 (1H, ddt, J=17.4, 10.2 and 5.2 Hz), 6.47 (1H, s), 7.05 (1H, dd, J=8.6 and 2.5 Hz), 7.30 (1H, d J=8.6 Hz), 7.38 (1H, s), 8.46 (1H, d, J=2.5 Hz).

Example 3

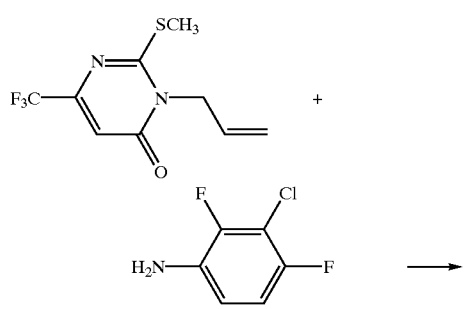

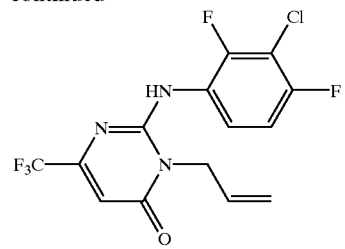

3-Allyl-2-methylthio-6-trifluoromethyl-4(3H)-pyrimidinone (1.50 g, 6.0 mmol) was dissolved in DMF (15 ml), and 3-chloro-2,-difluoroaniline (0.75 g, 4.6 mmol) was added. Then, sodium hydride (60% in oil, 0.30 g, 12.5 mmol) was added while stirring at 0° C., followed by stirring at 70° C. for 2.5 hours. After completion of the reaction, ether and saturated ammonium chloride aqueous solution were added to the reaction solution to effect phase separation. The organic layer was washed twice with a mixture of saturated brine/water (1/1) and then with saturated brine. Also, the aqueous layer was extracted with ether, and the ether layer was washed with the brine used for previous washing of the organic layer and saturated brine. The organic layers were combined and dried over anhydrous sodium sulfate. The drying agent was removed by filtration, and the resulting filtrate was concentrated under a reduced pressure. By purifying the thus obtained crude product by a silica gel column chromatography (hexane~hexane:ethyl acetate=9:1), 3-allyl-2-(3-chloro-2,4-difluorophenyl)amino-6-trifluoromethyl-4(3H)-pyrimidinone [Compound No. 8] was obtained as colorless crystals.

Yield: 80%; mp: 86–88° C.; $^1$H-NMR (CDCl$_3$, TMS, ppm): δ 4.85 (2H, dt, J=5.7 and 1.4 Hz), 5.51–5.61 (2H, m), 5.96 (1H, ddt, J=17.3, 10.4 and 5.7 Hz), 6.45 (1H, s), 7.04 (1H, ddd, J=9.4, 8.3 and 2.1 Hz), 7.09 (1H, s), 8.16 (1H, ddd, J=9.4, 8.7 and 5.4 Hz).

Example 4

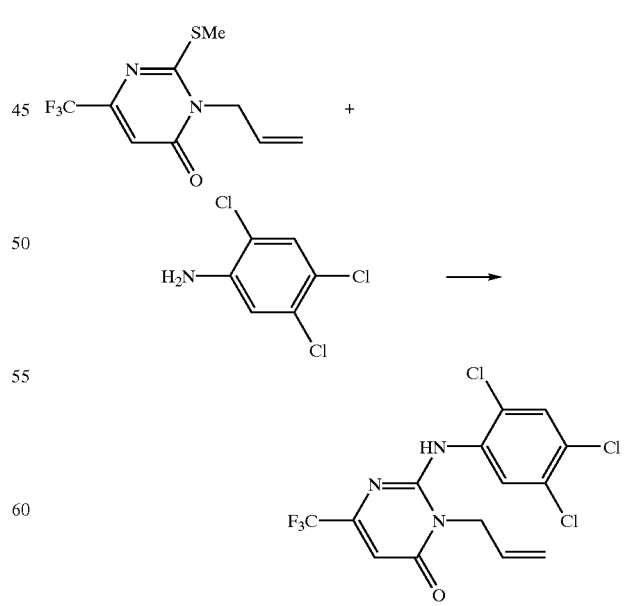

In accordance with the method of Example 1, white solid of 3-allyl-2-(2,4,-trichlorophenylamino)-6-trifluoromethyl- 4(3H)-pyrimidinone [Compound No. 15] was obtained by the reaction of 2,4,-trichloroaniline and 3-allyl-2-methylthio-6-trifluoromethyl-4(3H)-pyximidinone, Yield: 15%; mp: 145–147° C.; $^1$H-NMR (CDCl$_3$, TMS, ppm): δ 4.85 (2H, ddd, J=5.2, 1.7 and 1.7 Hz), 5.48 (1H, ddd, J=17.4, 1.7 and 1.7 Hz), 5.51 (1H, ddd, J=10.2, 1.7 and 1.7 Hz), 5.95 (1H, ddt, J=17.4, 10.2 and 5.2 Hz), 6.50 (1H, s), 7.32 (1H, br s), 7.50 (1H, s), 8.61 (1H, s).

Example 5

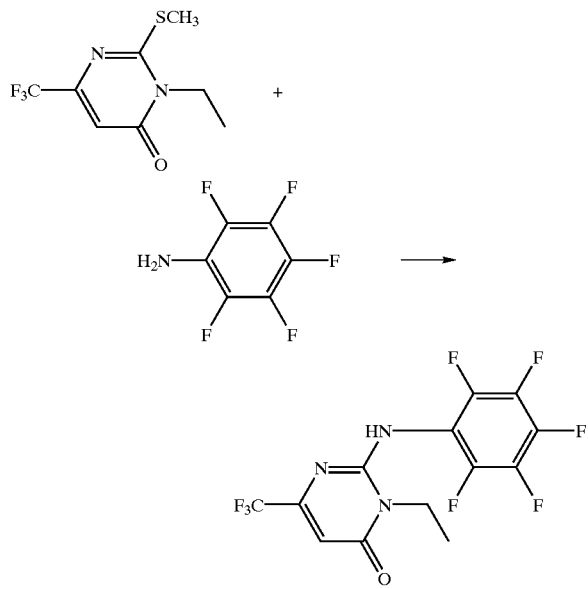

Sodium hydride (60% in oil, 0.44 g, 11.0 mmol) was added at room temperature to DMF, (8 ml) solution of 3-ethyl-2-methylthio-6-trifluoromethyl-4(3H)-pyrimidinone (2.27 g, 9.53 mmol) and pentafluoroaniline (1.10 g, 6.01 mmol.), followed by stirring for 3 hours. After completion of the reaction, ether (20 ml) and saturated ammonium chloride aqueous solution (10 ml) were added to the reaction solution to separate the organic layer and the resulting aqueous layer was extracted with ether (10 ml×2). The organic layers were combined, washed with saturated brine and then dried over anhydrous sodium sulfate. The drying agent was removed by filtration, and the resulting filtrate was concentrated under a reduced pressure. By purifying the thus obtained crude product by a silica gel column chromatography (hexane:ethyl acetate=3:1~1:1), white solid of 3-ethyl-2-(2,3,4,5,-pentafluorophenyl)amino-6-trifluoromethyl-4(3H)-pyrimidinone [Compound No. 16] was obtained.

Yield: 85.0%; mp: 146–149° C.: $^1$H-NMR (CDCl$_3$, TMS, ppm): δ 1.46 (3H, t,=7.3 Hz), 4.21 (2H, q, J=7.3 Hz), 6.20 (1H, br s), 6.42 (1H, s).

Example 6

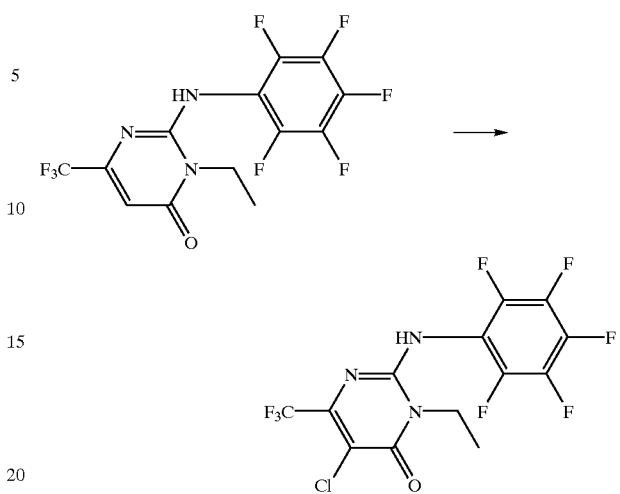

N-Chlorosuccinimide (0.61 g, 5.15 mmol) was added at room temperature to dichloromethane (15 ml) solution of 3-ethyl-2-(2,3,4,5,6-pentafluorophenyl)amino-6-trifluoromethyl-4(3H)-pyrimidinone (1.28 g, 3.42 mmol), followed by stirring at the same temperature for 24 hours. After completion of the reaction, ether (20 ml) and saturated ammonium chloride aqueous solution (10 ml) were added to the reaction solution to separate the organic layer, and the aqueous layer was extracted with ether (10 ml×2). The organic layers were combined, washed with saturated brine and then dried over anhydrous sodium sulfate. The drying agent was removed by filtration, and the resulting filtrate was concentrated under a reduced pressure. By purifying the thus obtained crude product by a silica gel column chromatography (hexane:ethyl acetate=3:1~1:1), white solid of 5-chloro-3-ethyl-2-(2,3,4,5,6-pentafluorophenyl) amino-6-trifluoromethyl-4 (3H)-pyrimidinone [Compound No. 17] was obtained.

Yield: 37.1; mp: 180–182° C.; $^1$H-NMR (CDCl$_3$, TMS, ppm): δ 1.49 (3H, t, J=7.3 Hz), 4.25 (2H, q, J=7.3 Hz), 6.05 (1H, br s).

Example 7

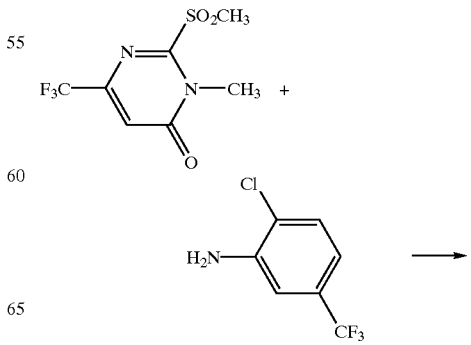

-continued

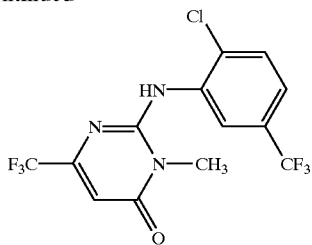

Sodium hydride (60% in oil, 468 mg, 11.7 mmol) was added to DMF, (30 ml) solution of 3-amino-4-chloxobenzotrifluoride (1.5 ml, 10.9 mmol), followed by stirring at room temperature for 30 minutes. Then, 3-methyl-2-methylsulfonyl-6-trifluoromethyl-4(3H)-pyximidinone (2 g, 7.8 mmol) was added, followed by stirring for 4 hours. After completion of the reaction, excess sodium hydride was neutralized with saturated ammonium chloride aqueous solution, ethyl acetate (70 ml) was added, and then the aqueous layer was removed. The organic layer was washed with water and saturated brine and then dried over anhydrous sodium sulfate. The solvent was evaporated under a reduced pressure, and purification by a silica gel column chromatography was carried out (hexane:ethyl acetate=3:1) to obtain yellow crystals of 2-(2-chloro-5-trifluoromethylphenyl)amino-3-methyl-6-trifluoromethyl-4(3H)-pyrimidinone [Compound No. 20].

Yield: 28%; mp: 158–159° C.: $^1$H NMR (CDCl$_3$, TMS, ppm): δ 3.68 (3H, s), 6.49 (1H, s), 7.36 (1H, dd, J=8.0 and 2.0 Hz), 7.39 (1H, s), 7.58 (1H, d, J=8.0 Hz), 8.96 (1H, d, J=2.0 Hz).

Example 8

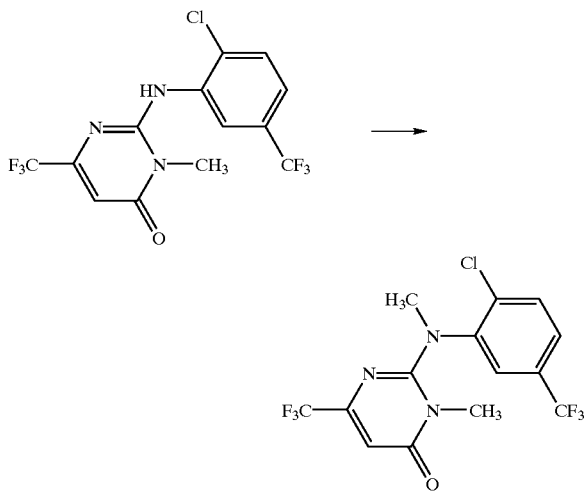

2-(2-Chloro-5-trifluoromethylphenyl) amino-3-methyl-6-trifluoromethyl-4(3H)-pyrimidinone (1.5 g, 4.0 mmol) was dissolved in DMF (10 ml), potassium carbonate (1.7 g, 12.0 mmol) and dimethyl sulfate (1.1 ml, 12.0 mmol) were added, followed by stirring at room temperature for 18 hours. After completion of the reaction, the reaction solution was diluted with ether (30 ml) and ice-water was added to separate the organic Layer, The organic layer was washed with saturated brine and water and then dried over anhydrous sodium sulfate. The drying agent was removed by filtration, and the filtrate was concentrated under a reduced pressure. By purifying the thus obtained crude product by a silica gel column chromatography (hexane:ethyl acetate= 10:1~2:1), 2-{N-(2-chloro-5-trifluoromethylphenyl)-N-methyl}amino-3-methyl-6-trifluoromethyl-4(3H)-pyrimidinone [Compound No. 21] was obtained as light brown crystals.

Yield: 14%; mp: 118–119° C.; $^1$H-NMR (CDCl$_3$, TMS, ppm): δ 2.93 (3H, s), 3.36 (3H, s), 6.55 (1H, s), 7.25 (1H, br s), 7.56 (1H, dd, J=8.4 and 1.9 Hz), 7.69 (1H, d, J=8.4 Hz).

Example 9

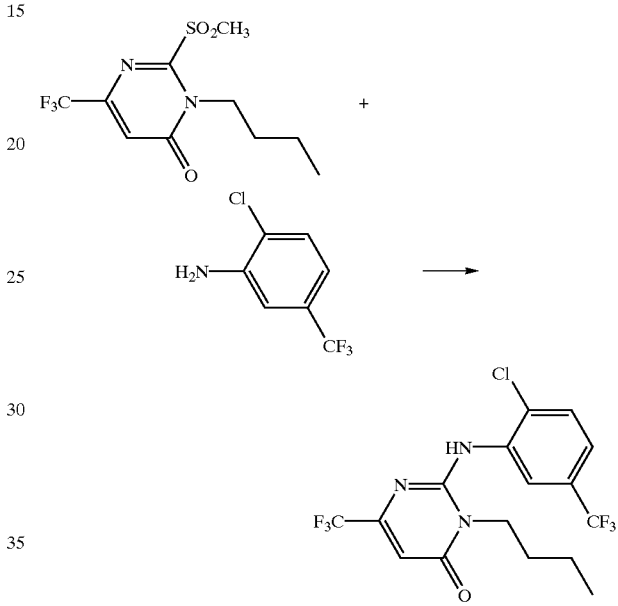

3-Amino-4-chlorobenzotrifluoride (2.9 g, 12.7 mmol) was dissolved in DMF (30 ml), sodium hydride (60% in oil, 540 mg, 13.5 mmol) was added, followed by stirring at room temperature for 30 minutes. Then, 3-butyl-2-methylsulfonyl-6-trifluoromethyl-4(3H)-pyrimidinone (3.0 g, 11.7 mmol) was added, followed by stirring for 4 hours. After completion of the reaction, the reaction solution was diluted with ether (20 ml), excess sodium hydride was neutralized with saturated ammonium chloride aqueous solution, and then the organic layer was separated and the resulting aqueous layer was extracted with ether (15 ml×2). The organic layers were combined, washed with saturated brine and then dried over anhydrous sodium sulfate. The drying agent was removed by filtration, and the resulting filtrate was concentrated under a reduced pressure. By purifying the thus obtained crude product by a silica gel column chromatography (hexane:ethyl acetate=10:1), 3-butyl-2-(3-chloro-5-trifluoromethylphenyl)amino-6-trifluoromethyl-4(3H)-pyrimidinone [Compound No. 22] was obtained as colorless crystals.

Yield: 5%; mp: 157–158° C.; $^1$H-NMR (CDCl$_3$, TMS, ppm): δ 1.04 (3H, t, J=7.2 Hz), 1.55 (2H, m), 1.84 (2H, m), 4.16 (2H, t, J=7.9 Hz), 6.46 (1H, s), 7.36 (1H, dd, J=8.3 and 1.6 Hz), 7.46 (1H, m), 7.56 (1H, d, J=8.3 Hz), 8.96 (1H, d, J=1.6 Hz).

Example 10

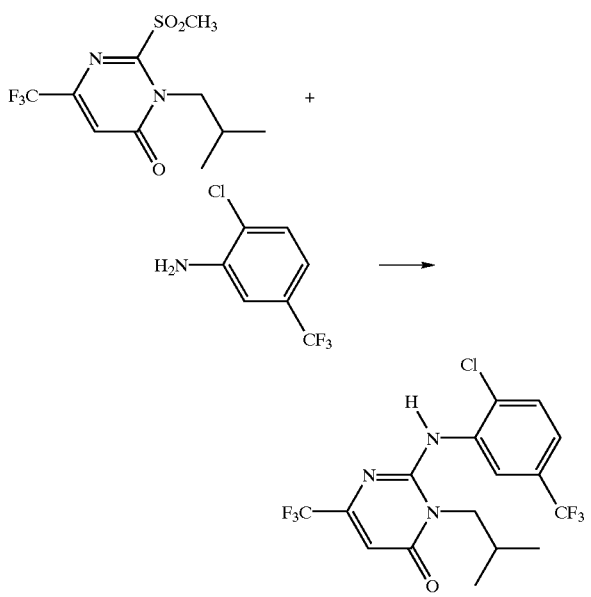

In accordance with the method of Example 7, 3-amino-4-chlorobenzotrifluoride was allowed to react with 3-isobutyl-2 methylsulfonyl-6-trifluoromethyl-4(3H)-pyrimidinone, thereby obtaining 2-(2-chloro-5-trifluoromethylphenyl)amino-3-isobutyl-6-trifluoromethyl-4(3H)-pyrimidinone [Compound No . 23].

Yield: 13%; mp: 118–119° C.; $^1$H-NMR (CDCl$_3$, TMS, ppm): δ 1.09 (6H, d, J=6.6 Hz), 2.20–2.40 (1H, m), 4.03 (2H, d, J=7.6 Hz), 6,48 (1H, s), 7.35 (1H, dd, J=8.0 and 2.0), 7.47 (1H, m), 7.56 (1H, d, J=8.0 Hz), 9.00 (1H, d, J=2.0 Hz).

Example 11

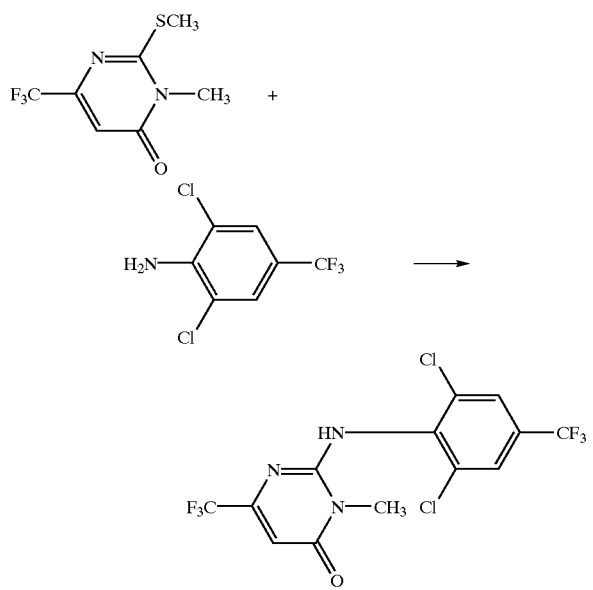

Sodium hydride (60% in oil, 0.31 g, 7.65 mmol) was added to DMF (5 ml) solution of 2,6-dichloro-4-trifluoromethylaniline (0.80 g, 3.48 mmol), followed by stirring for 30 minutes. Then, 3-methyl-2-methylthio-6-trifluoromethyl-4(3H)-pyrimidinone (0.70 g, 3.13 mmol) was added, followed by stirring at 50° C. for 8 hours. After completion of the reaction, 1 N hydrochloric acid (30 ml) and ethyl acetate (20 ml) were added to the reaction solution to separate the organic layer, and the resulting aqueous layer was extracted with ethyl acetate (50 ml). The organic layers were combined, washed with water (30 ml×2) and saturated brine (70 ml) and then dried over anhydrous magnesium sulfate. The drying agent was removed by filtration, and the resulting filtrate was concentrated under a reduced pressure. By recrystallizing the thus obtained crude product from toluene and then from chloroform, white solid of 2-(2,6-dichloro-4-trifluoromethylphenyl)amino-3methyl-6-trifluoromethyl-4(3H)-pyrimidinone [Compound No. 28] was obtained.

Yield: 40%; mp: 212–213° C.; $^1$H-NMR (CDCl$_3$, TMS, ppm): δ 3.65 (3H, s), 6.36 (1H, s), 7. 69 (2H, s), 7. 85 (1H, br s).

Example 12

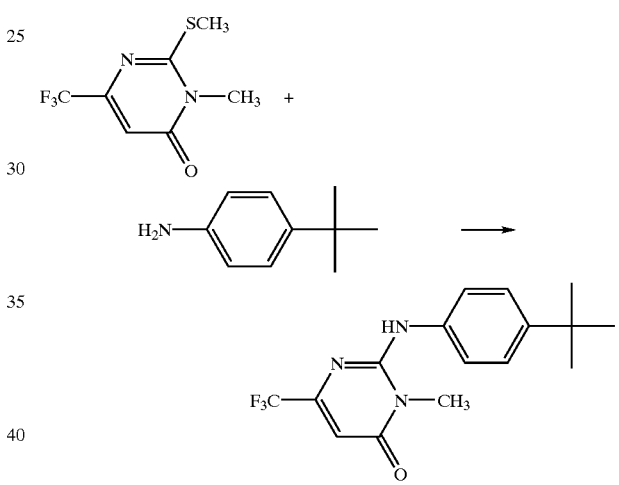

Sodium hydride (60% in oil, 0.15 g, 3.75 mmol) was added at room temperature to DMF (5 ml) solution of 4-tert-butylaniline (0.47 g, 3.13 mmol), followed by stirring for 30 minutes. Then, 3-methyl-2-methylthio-6-trifluoromethyl-4(3H)-pyrimidinone (0.80 g, 3.13 mmol) was added, followed by stirring at room temperature for 7 hours. After completion of the reaction, 1 N hydrochloric acid (30 ml) and ethyl acetate (20 ml) were added to separate the organic layer, and the resulting aqueous layer was extracted with ethyl acetate (50 ml). The organic layers were combined, washed with water (30 ml×2) and saturated brine (70 ml) and then dried over anhydrous magnesium sulfate. The drying agent was removed by filtration, the resulting filtrate was concentrated under a reduced pressure. By purifying the thus obtained crude product by a silica gel column chromatography (hexane:ethyl acetate=7:3), white solid of 2-(3tert-butylphenyl)amino-3-methyl-6-trifluoroethyl-4(3H)-pyrimidinone [Compound No. 30] was obtained.

Yield: 39%; $^1$H-NMR (CDCl$_3$, TMS, ppm): δ 1.33 (9H, s), 3.58 (3H, s), 6.37 (1H, S), 6.5 (1H, br s), 7.2 (4H, m)

Example 13

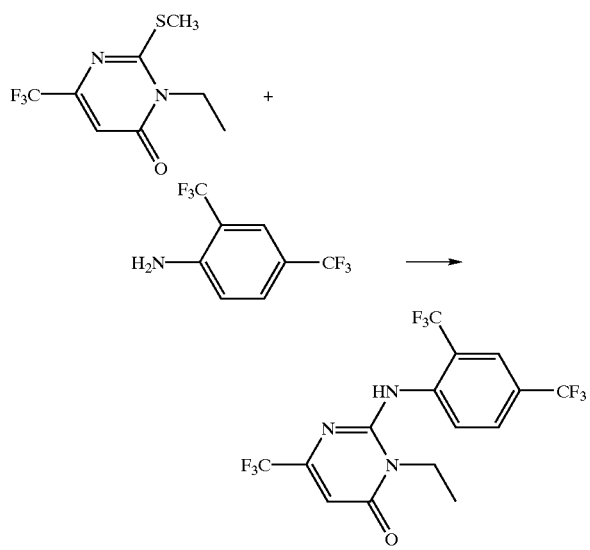

Sodium hydride (60% in oil, 0.45 g, 11.4 mmol) was added to DMF (5 ml) solution of 2,4-bis(trifluoromethyl) aniline (2.00 g, 8.73 mmol), followed by stirring for 30 minutes. Then, 3-ethyl-2-methylthio-6-trifluoromethyl-4 (3H)-pyrimidinone (2.08 g, 8.73 mmol) was added, followed by stirring at 60° C. for 2 hours. After completion of the reaction, 1 N hydrochloric acid (30 ml) and ethyl acetate (20 ml) were added to the reaction solution to separate the organic layer, and the resulting aqueous layer was extracted with ethyl acetate (50 ml). The organic layers were combined, washed with water (30 ml×2) and saturated brine (70 ml) and then dried over anhydrous magnesium sulfate. The drying agent was removed by filtration, and the resulting filtrate was concentrated under a reduced pressure. By purifying the thus obtained crude product by a silica gel column chromatography (hexane:ethyl acetate=9:1~7:3), white solid of 2-{2,4-bis(trifluoromethyl)phenyl}amino-3-ethyl-6-trifluoromethyl-4(3H)-pyrimidinone [Compound No. 33] was obtained.

Yield: 35%; mp: 112–114° C.; $^1$H-NMR (CDCl$_3$, TMS, ppm): δ 1.46 (3H, t, J=7.5 Hz), 4.18 (2H, q, J=7.5 Hz), 6,48 (1H, s), 7.24 (1H, br s), 7.90 (1H, d, J=9.0 Hz), 7,92 (1H, s), 8.52 (1H, d, J=9.0 Hz).

Example 14

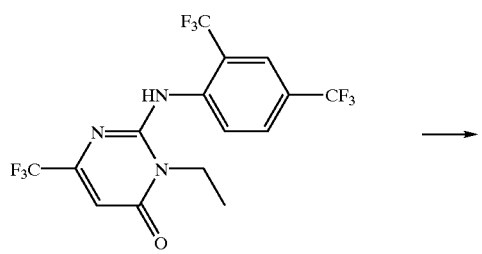

-continued

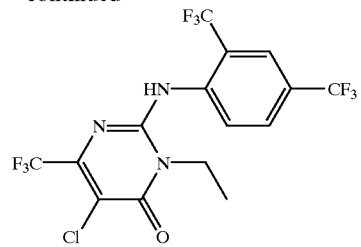

Sulfuryl chloride (0.36 g, 2.68 mmol) was added to dichloromethane (30 ml) solution of 3-{2,4-bis (trifluoromethyl)phenyl}amino-3-ethyl-6-trifluoromethyl-4 (3H)-pyrimidinone (0.75 g, 1.79 mmol), followed by stirring at room temperature for 2 hours. After completion of the reaction, the reaction solution was concentrated under a reduced pressure, and the thus obtained crude product was washed with (hexane: to obtain white solid of 2-{2,4-bis (trifluoromethyl)phenyl}amino-5-chloro-3-ethyl-6-trifluoromethyl-4(3H)-pyrimidinone [Compound No. 34].

Yield: 41%; mp: 124° C.; $^1$H-NMR (CDCl$_3$, TMS, Ppm): δ 1.49 (3H, t, J=7.5 Hz), 4.22 (2H, q, J=7.5 Hz), 7.20 (1H, br s), 7.91 (1H, d, J=9.0 Hz), 7.93 (1H, s), 8.56 (1H, d, J=9.0 Hz).

Example 15

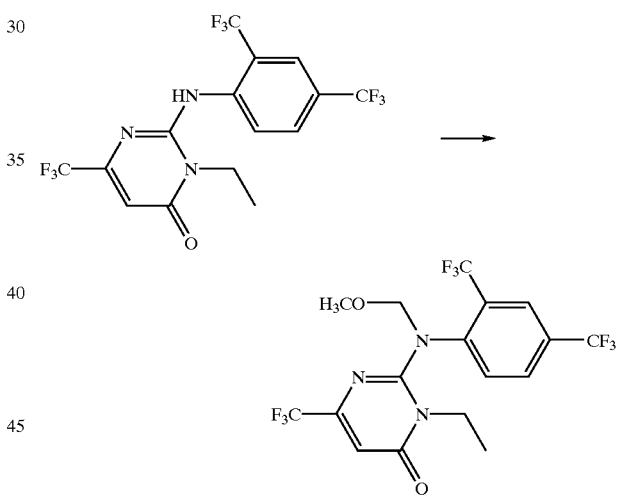

To acetonitrile (40 ml) solution of 2-{2,4-bis (trifluoromethyl)phenyl}amino-3-ethyl-6-trifluoromethyl-4 (3H)-pyrimidinone (1.68 g, 4.0 mmol) were added 18-crown-6-ether (0.11 g, 0.4 mmol) and then potassium carbonate (3.96 g, 28.8 mmol) and chloromethyl methyl ether (2.16 ml, 28.8 mmol) in six portions, followed by stirring at 80° C. for 7 hours. After completion of the reaction, water (40 ml) and ethyl acetate (40 ml) were added to the reaction solution to separate the organic layer, and the aqueous layer was extracted with ethyl acetate (20 ml×3). The organic layers were combined, washed with water (80 ml×2) and saturated sodium chloride aqueous solution (100 ml) and then dried over anhydrous magnesium sulfate. The drying agent was removed by filtration, and the resulting filtrate was concentrated under a reduced pressure. By purifying the thus obtained crude produce by a silica gel column chromatography (ethyl acetate:hexane=1.6), colorless and transparent viscous oil of 2-{N-2,4-bis (trifluoromethyl)phenyl-N-methoxymethyl}amino-3-ethyl-6-trifluoromethyl-4-(3H)-pyrimidinone [Compound No. 36] was obtained.

Yield: 17%; $^1$H-NMR (CDCl$_3$, TMS, ppm): δ1.03 (3H, t, J=7.0 Hz), 3.42 (3H, s), 3.88 (2H, q, J=7.0 Hz), 5.12 (2H, s), 6.57 (1H, s), 7.60 (1H, d, J=8.4 Hz), 7.89 (1H, d, J=8.4 Hz), 8.01 (1H, s).

Example 16

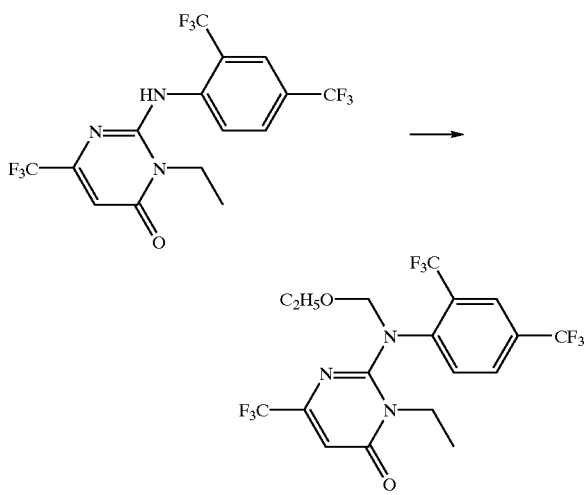

To acetonitrile (50 ml) solution of 2-{2,4-bis(trifluoromethyl)phenyl}amino-3-ethyl-6-trifluoromethyl-4(3H)-pyrimidinone 1.26 g, 3.0 mmol) were added 18-crown-6-ether (0.08 g, 0.3 mmol) and then potassium carbonate (3.0 g, 21.6 mmol) and chloromethyl ethyl ether (1.86 ml, 21.6 mmol) in six portions, followed by stirring at 80° C. for 16.5 hours. After completion of the reaction, water (50 ml) and ethyl acetate (50 ml) were added to separate the organic layer, and the resulting aqueous layer was extracted with ethyl acetate (30 ml×3). The organic layers were combined, washed with water (80 ml×2) and saturated sodium chloride aqueous solution (100 ml) and then dried over anhydrous magnesium sulfate. The drying agent was removed by filtration, and the resulting filtrate was concentrated under a reduced pressure. By purifying the thus obtained crude product by a silica gel column chromatography (ethyl acetate:hexane=1:10), while solid of 2-{2,4-bis(trifluoromethyl)phenyl-N-ethyoxymethyl}amino-3-ethyl-6-trifluoromethyl-4(3H)-pyrimidinone [Compound No. 37] was obtained.

Yield: 55%; mp: 51–52° C.; $^1$H-NMR (CDCl$_3$, TMS, ppm): δ1.03 (3H, t, J=7.0 Hz), 1.18 (3H, t, J=7.0 Hz), 3.61 (2H, q, J=7.0 Hz), 3.88 (2H, q, J=7.0 Hz), 5.17 (2H, s), 6.55 (1H, s), 7.64 (1H, d, J=8.4 Hz), 7.89 (1H, d, J=8.4 Hz), 8.00 (1H, s).

Example 17

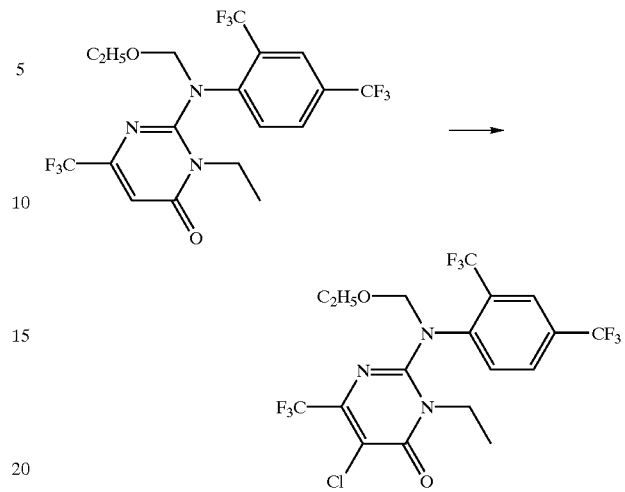

While stirring under ice-cooling, sulfuryl chloride (0.50 g, 3.6 mmol) was added to dichloromethane (5 ml) solution of 2-{N-2,4-bis(trifluoromethyl)phenyl-N-ethoxymethyl}amino-3-ethyl-6-trifluoromethyl-4(3H)-pyrimidinone (1.26 g, 3.0 mmol), and it was stirred at 0° C. for 30 minutes, gradually returned to room temperature, and then stirred for 2.5 hours. After completion of the reaction, water (10 ml) and ethyl acetate (10 ml) were added to the reaction solution to separate the organic layer, and he resulting aqueous layer was extracted with ethyl acetate (5 ml×2). The organic layers were combined, washed with saturated sodium chloride aqueous solution (20 ml) and then dried over anhydrous magnesium sulfate. The drying agent was removed by filtration, and the resulting filtrate was concentrated under a reduced pressure. By purifying the thus obtained crude product by a silica gel thin layer chromatography (toluene), light yellow oil of 2-{N-2,4-bis(trifluoromethyl)phenyl-N-ethoxymethyl}amino-5-chloro-3-ethyl-6-trifluoromethyl-4(3H)-pyrimidinone [Compound No. 38] was obtained.

Yield: 10%; $^1$H-NMR (CDCl$_3$, TMS, ppm): δ1.10 (3H, t, J=7.0 Hz), 1.19 (3H, t, J=7.0 Hz), 3.59 (2H, q, J=7.0 Hz), 3.96 (2H, q, J=7.0 Hz), 5.14 (2H, s), 7.67 (1H, d, J=8.5 Hz), 7.91 (1H, d, J=8.5 Hz), 8.01 (1H, s).

Example 18

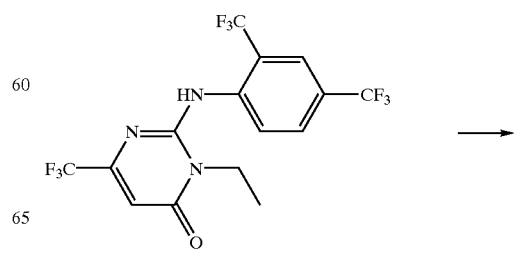

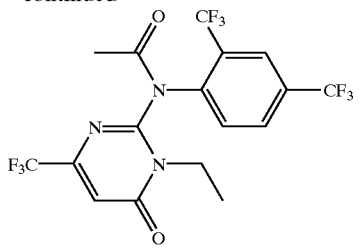

A catalytically effective amount of pyridine was added to acetic anhydride (10 ml) solution of 2-{2,4-bis(trifluoromethyl)phenyl}amino-3-ethyl-6-trifluoromethyl-4(3H)-pyrimidinone (0.27 g, 0.64 mmol), followed by stirring at 100° C., for 8 hours. After completion of the reaction, water (10 ml) and ethyl acetate (10 ml) were added to the reaction solution to separate the organic layer, and the resulting aqueous layer was extracted with ethyl acetate (10 ml×3). The organic layers were combined, washed with water (30 ml×2 ml) and saturated sodium chloride aqueous solution (40 ml), and then dried over anhydrous magnesium sulfate. The drying agent was removed by filtration, and the resulting filtrate was concentrated under a reduced pressure. By purifying the thus obtained crude product by a silica gel column chromatography (ethyl acetate:hexane=1:10), white solid of 2-{N-acetyl-N-2,4-bis(trifluoromethyl)-phenyl}amino-3-ethyl-6-trifluoromethyl-4(3H)-pyrimidinone [Compound No. 39] was obtained.

Yield: 80%; mp: 92–94° C., $^1$H-NMR (CDCl$_3$, TMS, ppm): δ1.44 (3H, m, 3H), 2.06 (3H, br s), 4.04–4.06 (2H, m), 6.69 (1H, br s), 7.86–8.05 (3H, m)

Example 19

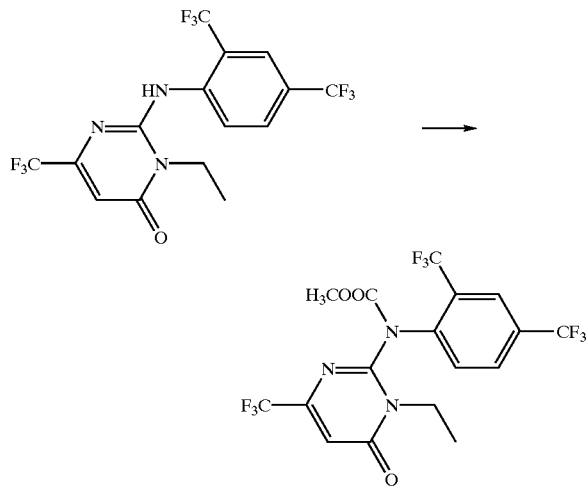

To acetonitrile (20 ml) solution of 2-{2,4-bis(trifluoromethyl)phenyl}amino-3-ethyl-6-trifluoromethyl-4(3H)-pyrimidinone (1.26 g, 3.0 mmol), were added 18-crown-6-ether (0.08 g, 0.3 mmol) and then potassium carbonate (3.0 g, 21.6 mmol) and methyl chloroformate (1.4 ml, 21.6 mmol) in six portions, followed by stirring at 80° C. for 27.5 hours. After completion of the reaction, water (20 ml) and ethyl acetate (20 ml) were added to the reaction solution to separate the organic layer, and the resulting aqueous layer was extracted with ethyl acetate (10 ml×3). The organic layers were combined, washed with water (50 ml×2) and saturated sodium chloride aqueous solution (60 ml), and then dried over anhydrous magnesium sulfate. The drying agent was removed by filtration, and the resulting filtrate was concentrated under a reduced pressure. By purifying the thus obtained crude product by a silica gel column chromatography (ethyl acetate:hexane=1:6), white solid of 2-{N-2,4-bis(trifluoromethyl)phenyl-N-methoxycarbonyl}amino-3-ethyl-6-trifluoromethyl-4(3H)-pyrimidinone [Compound No. 40] was obtained.

Yield: 44%; mp: 56–58° C.; $^1$H-NMR (CDCl$_3$, TMS, ppm): δ1.42 (3H, t, J=7.0 Hz), 3.84 (3H, s), 4.05–4.16 (2H, m), 6.71 (1H, s), 7.75 (1H, d, J=8.4 Hz), 7.92–7.99 (2H, m).

Example 20

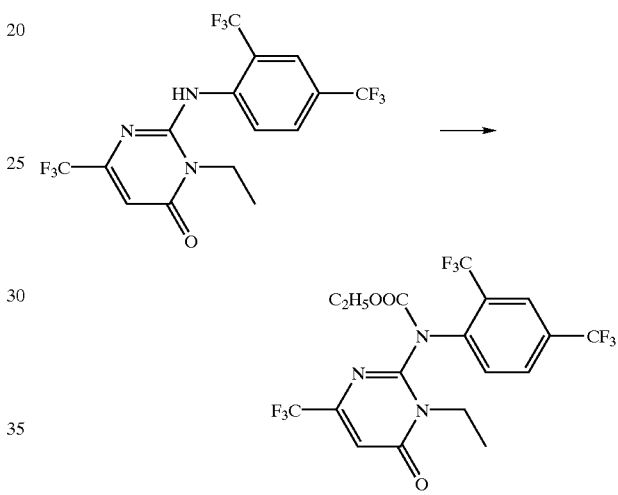

To acetonitrile (20 ml) solution of 2-{2,4-bis(trifluoromethyl)phenyl}amino-3-ethyl-6-trifluoromethyl-4(3H)-pyrimidinone (0.84 g, 2.0 mmol) were added 18-crown-6-ether (0.05 g, 0.2 mmol) and then potassium carbonate (1.98 g, 14.4 mmol) and ethyl chloroformate (1.38 ml, 14.4 mmol) in six portions, followed by stirring at 80° C. for 20 hours. After completion of the reaction, water (20 ml) and ethyl acetate (20 ml) were added to the reaction solution to separate the organic layer, and the resulting aqueous layer was extracted with ethyl acetate (10 ml×3). The organic layers were combined, washed with water (50 ml×2) and saturated sodium chloride aqueous solution (60 ml), and then dried over anhydrous magnesium sulfate. The drying agent was removed by filtration, and the resulting filtrate was concentrated under a reduced pressure. By purifying the thus obtained crude product by a silica gel column chromatography (ethyl acetate:hexane=1:8), white solid of 2-{N-2,4-bis(trifluoromethyl)phenyl-N-ethoxycarbonyl}amino-3-ethyl-6-trifluoromethyl-4(3H)-pyrimidinone [Compound No. 41] was obtained.

Yield: 30%; mp: 48–50° C.; $^1$H-NMR (CDCl$_3$, TMS, ppm): δ1.22–1.29 (3H, m), 1.42 (3H, t, J=7.1 Hz, 3H), 4.10–4.14 (2H, m), 4.30 (2H, q, J=7.1 Hz), 6.71 (1H, s), 7.74 (1H, d, J=8.3 Hz), 7.93 (1H, d, J=8.3 Hz), 7.99 (1H, s).

Example 21

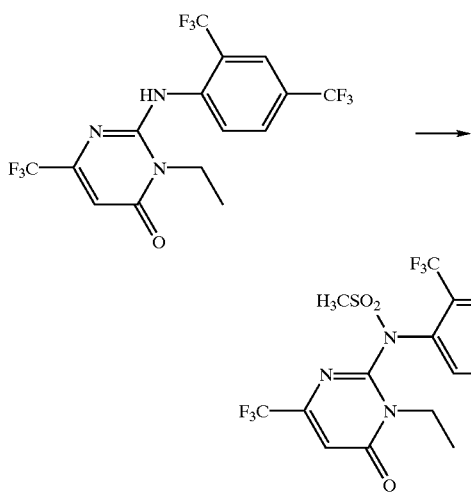

To acetonitrile (20 ml) solution of 2-{2,4-bis(trifluoromethyl)phenyl}amino-3-ethyl-6-trifluoromethyl-4(3H)-pyrimidinone (0.84 g, 2.0 mmol) were added 18-crown-6-ether (0.05 g, 0.2 mmol) and then potassium carbonate (1.32 g, 9.6 mmol) and methanesulfonyl chloride (0.76 ml, 9.6 mmol) in four portions, followed by stirring at 80° C. for 6 hours. After completion of the reaction, water (20 ml) and ethyl acetate (20 ml) were added to the reaction solution to separate the organic layer, and the resulting aqueous layer was extracted with ethyl acetate (10 ml×3). The organic layers were combined, washed with water (50 ml×2) and saturated sodium chloride aqueous solution (60 ml), and then dried over anhydrous magnesium sulfate. The drying agent was removed by filtration, and the resulting filtrate was concentrated under a reduced pressure. By purifying the thus obtained crude product by a silica gel column chromatography (ethyl acetate:hexane=1:8), colorless and transparent oil of 2-{N-2,4-bis(trifluoromethyl)phenyl-N-methylsulfonyl}amino-3-ethyl-6-trifluoromethyl-4(3H)-pyrimidinone [Compound No. 43] was obtained.

Yield: 28%, $^1$H-NMR (CDCl$_3$, TMS, ppm): δ1.01 (3H, t, J=7.3 Hz), 3.46 (3H, s), 4.06 (2H, q, J=7.3 Hz), 6.81 (1H, s), 7.97–8.13 (3H, m).

Example 22

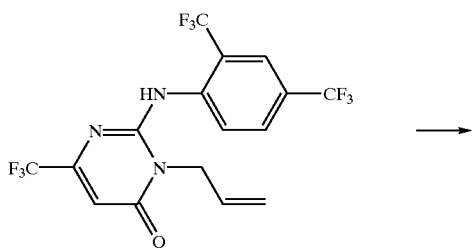

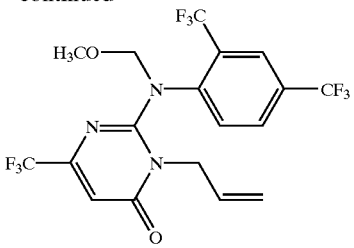

To acetonitrile (20 ml) solution of 2-{2,4-bis(trifluoromethyl)phenyl}amino-3-allyl-6-trifluoromethyl-4(3H)-pyrimidinone (1.0 g, 2.32 mmol) synthesized in accordance with the method of Example 1 by the reaction of 2,4-bis(trifluoromethyl)aniline with 3-allyl-2-methylthio-6-trifluoromethyl-4(3H)-pyrimidinone were added potassium carbonate (1.28 g, 9.28 mmol), chloromethyl methyl ether (748 mg, 9.28 mmol) and 18-crown-6-ether (56 mg), followed by heating under reflux for 9 hours. After completion of the reaction, water (50 ml) and ethyl acetate (50 ml) were added to the reaction solution to separate the organic layer, and the resulting aqueous layer was extracted with ethyl acetate (50 ml). The organic layers were combined, washed with water (50 ml×3) and then dried over anhydrous magnesium sulfate. The drying agent was removed by filtration, and the resulting filtrate was concentrated under a reduced pressure. By purifying the thus obtained crude product by a silica gel column chromatography (ethyl acetate:hexane=1:5), yellow oil of 2-{N-2,4-bis(trifluoromethyl)phenyl-N-methoxymethyl}amino-3-allyl-6-trifluoromethyl-4(3H)-pyrimidinone [Compound No. 45] was obtained.

Yield: 24.4%; $^1$H-NMR, (CDCl$_3$, TMS, ppm): δ3.38 (3H, s), 4.54 (2H, ddd, J=4.8, 1.8 and 1.7 Hz), 4.93 (1H, dt, J=17.4 and 1.7 Hz), 5.05 (1H, dt, J=10.7 and 1.8 Hz), 5.10 (2H, s), 5.68 (1H, ddt, J=17.4, 10.7 and 4.8), 6.57 (1H, s), 7.69 (1H, d, J=8.4 Hz), 7.89 (1H, dd, J=8.4 and 1.6 Hz), 7.97 (1H, d, J=1.6 Hz).

Example 23

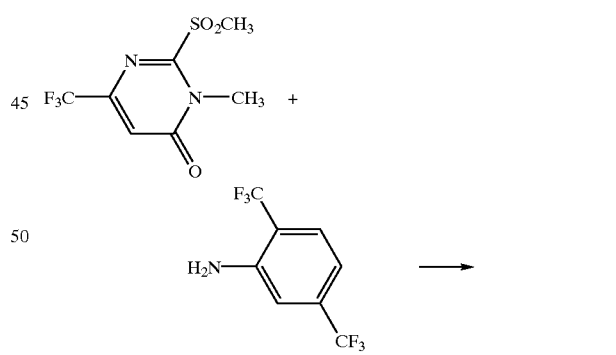

Sodium hydride (60% in oil, 468 mg, 17.6 mmol) was added to DMF (30 ml) solution of 2,5-bis(trifluoromethyl)

aniline (3.8 g, 16.4 mmol), followed by stirring at room temperature for 30 minutes. Then, 3-methyl-2-methylsulfonyl-6-trifluoromethyl-4(3H)-pyrimidinone (3.0 g, 11.7 mmol) was added, followed by stirring for additional 4 hours. After completion of the reaction, the reaction solution was diluted with ether (20 ml), excess sodium hydride was neutralized with saturated ammonium chloride aqueous solution and then the aqueous layer was separated. After extraction of the aqueous layer with ether (20 ml×2), the organic layers were combined, washed with saturated brine and then dried over anhydrous sodium sulfate. The solvent was evaporated under a reduced pressure, and the resulting residue was purified by a silica gel column chromatography (hexane:ethyl acetate=20:1~8:1) to obtain light yellow crystals of 2-{2,5-bis(trifluoromethyl)phenyl}amino-3-methyl-6-trifluoromethyl-4(3H)-pyrimidinone [Compound No. 46].

Yield: 25% mp: 155–156° C.; $^1$H-NMR, (CDCl$_3$, TMS, ppm): δ 3.62 (3H, s), 6.48 (1H, s), 7.10 (1H, br s), 7.57 (1H, d, J=8.2 Hz), 7.81 (1H, d, J=8.2 Hz), 8.72 (1H, s).

Example 24

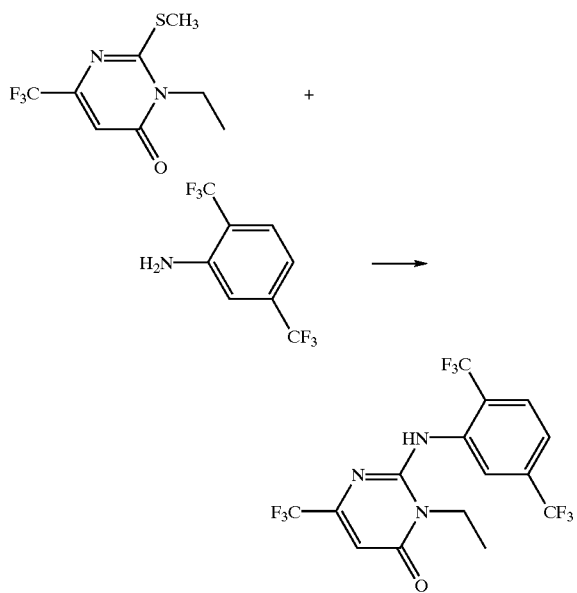

Sodium hydride (60% in oil, 0.97 mg, 14.6 mmol) was added to DMF (45 ml) solution of 2,5-bis(trifluoromethyl)aniline (0.58 g, 14.6 mmol), followed by stirring for 20 minutes. Then, 3-ethyl-2-methylthio-6-trifluoromethyl-4(3H)-pyrimidinone (3.32 g, 14.0 mmol) was added, followed by stirring at 80° C. for 4 hours. After completion of the reaction, ice-water (50 ml) and ethyl acetate (30 ml) were added to the reaction solution to separate the organic layer, and the resulting aqueous layer was extracted with ethyl acetate (20 ml×3). The organic layers were combined, washed with saturated sodium bicarbonate aqueous solution (50 ml), water (50 ml×2) and saturated brine (80 ml), and then dried over anhydrous magnesium sulfate. The drying agent was removed by filtration, and the resulting filtrate was concentrated under a reduced pressure. The thus obtained crude product was purified by a silica gel column chromatography (ethyl acetate:hexane=1:10) and then recrystallized from toluene, thereby obtaining 2-{2,5-bis(trifluoromethyl)phenyl}amino-3-ethyl-6-trifluoromethyl-4(3H)-pyrimidinone [Compound No. 47].

Yield: 27%; mp: 173–175° C.; $^1$H-NMR (CDCl$_3$, TMS, ppm): δ 1.45 (3H, t, J=7.35 Hz), 4.16(2H, q, J=7.35 Hz), 6.46 (1H, s), 7.17 (1H, br s), 7.55 (1H, d, J=8.24 Hz), 7.81 (1H, d, J=8.25 Hz), 8.73 (1H, br s).

Example 25

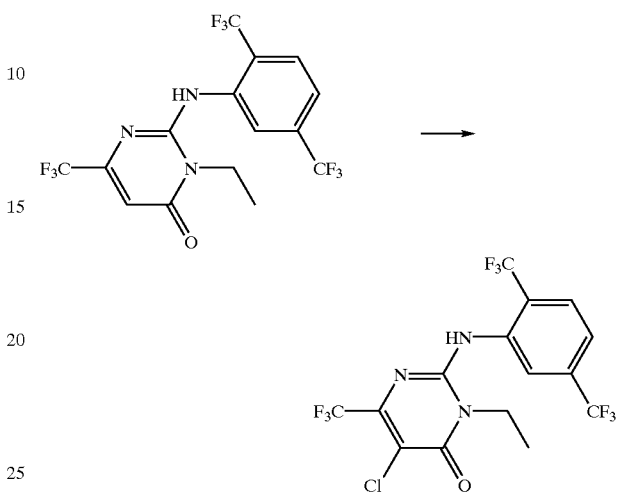

While stirring under ice-cooling, 10% hexane solution of sulfuryl chloride (0.019 ml, 0.24 mmol) was added to acetic acid (3 ml) solution of 2-{2,5-bis(trifluoromethyl)phenyl}amino-3-ethyl-6-trifluoromethyl-4(3H)-pyrimidinone (0.10 g, 0.24 mmol), followed by stirring for 1.5 hours while gradually returning to room temperature. After completion of the reaction, ice-water (10 ml) and ether (10 ml) were added to the reaction solution to separate the organic layer, and the resulting aqueous layer was extracted with ether (10 ml×3). The organic layers were combined, washed with water (20 ml×2) and then dried over anhydrous magnesium sulfate. The drying agent was removed by filtration, and the resulting filtrate was concentrated under a reduced pressure. By recrystallizing the thus obtained crude product from chloroform/hexane, 2-{2,5-bis(trifluoromethyl)phenyl}amino-5-chloro-3-ethyl-6-trifluoromethyl-4(3H)-pyrimidinone [Compound No. 49] was obtained.

Yield: 53.2%; mp: 144–146° C.; $^1$H-NMR (CDCl$_3$, TMS, ppm): δ 1.48 (3H, t, J=7.35 Hz), 4.22 (2H, q, J=7.35 Hz), 7.14 (1H, br s), 7.57 (1H, d, J=8.25 Hz), 7.62 (1H, d, J=8.25 ), 8.77 (1H, br s).

Example 26

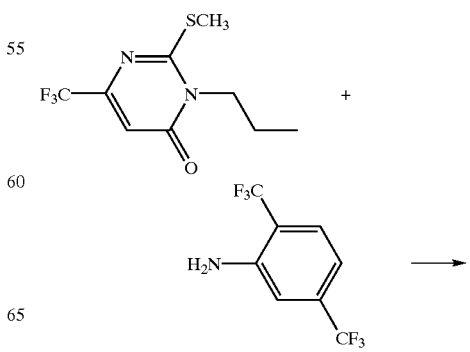

-continued

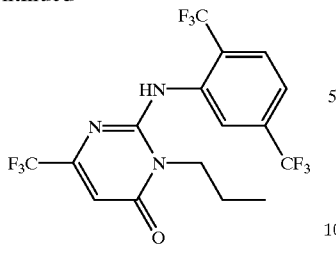

In accordance with the method of Example 24, 2-methylthio-3-propyl-6-trifluoromethyl-4(3H)-pyrimidinone (1.76 g, 6.98 mmol) and 2,5-bis(trifluoromethyl)aniline (1.0 g, 4.36 mmol) were allowed to react with sodium hydride (60% in oil, 0.48 g, 7.28 mmol) in DMF (20 ml) at 80° C. for 4 hours, thereby obtaining 2-{(2,5-bis(trifluoromethyl)phenyl}amino-3-propyl-6-trifluoromethyl-4(3H)-pyrimidinone [Compound No. 50 ].

Yield: 54.5%; mp: 127–129° C.; $^1$H-NMR (CDCl$_3$, TMS, ppm): δ 1.10 (3H, t, J=7.4 Hz), 1.81 (2H, tq, J=8.1 and 7.4 Hz), 4.05 (2H, t, J=8.1 Hz), 6.47 (1H, s), 7.18 (1H, br s), 7.54 (1H, d, J=8.2 Hz), 7.80 (1H, d, J=8.2 Hz), 8.79 (1H, s).

Example 27

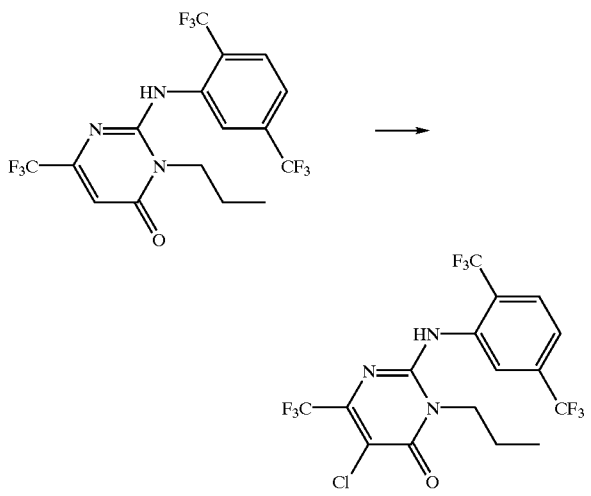

In accordance with the method of Example 25, chlorination of 2-{2,5-bis(trifluoromethyl)phenyl}amino-3-propyl-6-trifluoromethyl-4(3H)-pyrimidinone (80 mg, 0.18 mmol) was carried out using sulfuryl chloride, thereby obtaining 2-{2,5-bis(trifluoromethyl)phenyl}amino-5-chloro-3-propyl-6-trifluoromethyl-4(3H)-pyrimidinone [Compound No. 51].

Yield: 78.3%; mp: 124–126° C.; $^1$H-NMR (CDCl$_3$, TMS, ppm): δ 1.12 (3H, t, J=7.43 Hz), 1.86 (2H, tq, J=8.14 and 7.43 Hz), 4.09 (2H, t, J=8.14 Hz), 7.12 (1H, br s), 7.54 (1H, d, J=8.25 Hz), 7.81 (1H, d, J=8.25 Hz), 8.82 (1H, br s).

Example 28

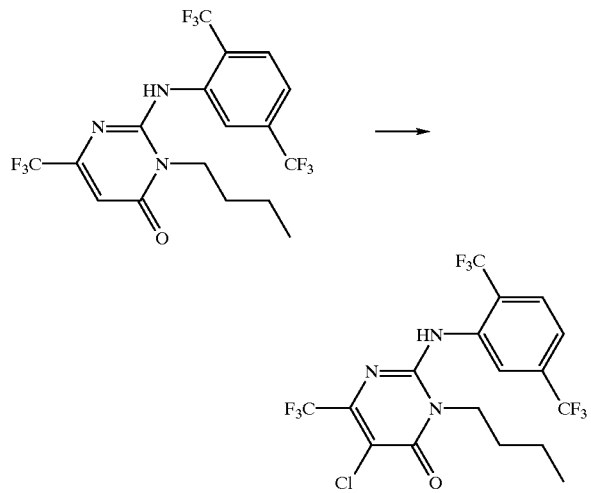

Sulfuryl chloride (0.011 ml) was added to acetic acid (1.3 ml) solution of 2-{2,5-bis(trifluoromethyl)phenyl}amino-3-butyl-6-trifluoromethyl-4(3H)-pyrimidinone (60 mg, 0.13 mmol) which had been synthesized in accordance with the method of Example 24, followed by stirring at room temperature for 1 hour. After completion of the reaction, ether (20 ml) was saturated sodium bicarbonate aqueous solution (20 ml) were added to the reaction solution to separate the organic layer, and the resulting aqueous layer was extracted with ether (10 ml×2). The thus obtained ether layers were combined, washed with sodium bicarbonate aqueous solution (20 ml) and saturated brine (20 ml), dried over anhydrous sodium sulfate, and then the solvent was evaporated under a reduced pressure. By purifying the thus obtained crude product by a silica gel column chromatography (dichloromethane:hexane=10:3), white solid of 2-{2,5-bis(trifluoromethyl)phenyl}amino-3-butyl-5-chloro-6-trifluoromethyl-4(3H)-pyrimidinone [Compound No. 55] was obtained.

Yield: 90%; mp: 121–122° C.; $^1$H-NMR (CDCl$_3$, TMS, ppm): δ 1.04 (3H, t, J=7.4 Hz), 1.47–158 (2H, m), 1.75–185 (2H, m), 4.13 (2H, dd, J=8.3 and 8.1 Hz), 7.15 (1H, s), 7.56 (1H, d, J=8.2 Hz), 7.82 (1H, d, J=8.2 Hz), 8.80 (1H, s), Example 29

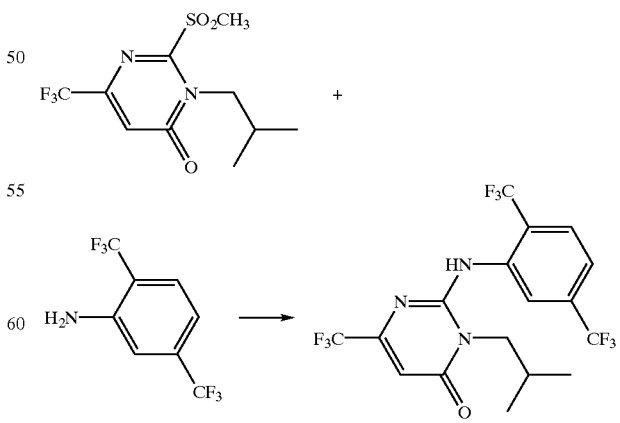

Sodium hydride (60% in oil, 1.01 g, 15.2 mmol) was added to DMF (30 ml) solution of 2,5-bis(trifluoromethyl)

aniline (3.2 g, 14.1 mmol), followed by stirring at room temperature for 30 minutes. Then, 3-isobutyl-2-methylsulfonyl-6-trifluoromethyl-4(3H)-pyrimidinone (3.0 g, 11.7 mmol) was added, followed by further stirring for 4 hours. After completion of the reaction, the reaction solution was diluted with ether (20 ml), excess sodium hydride was neutralized with saturated ammonium chloride aqueous solution (20 ml), and then the aqueous layer was separated. After extraction of the aqueous layer with ether (20 ml×2), the organic layers were combined, washed with saturated brine (10 ml), and then dried over anhydrous sodium sulfate. The drying agent was removed by filtration, and the solvent was evaporated from the resulting filtrate under a reduced pressure. By purifying the thus obtained crude product by a silica gel column chromatography (hexane:ethyl acetate= 20:1), 2-{2,5-bis(trifluoromethyl)phenyl}amino-3-isobutyl-6-trifluoromethyl-4(3H)-pyrimidinone [Compound No. 56] was obtained as colorless crystals.

Yield: 29%; mp: 136–138° C.; $^1$H-NMR (CDCl$_3$, TMS, ppm): δ 1.06 (6H, d, J=6.6 Hz), 2.18 (1H, m), 3.97 (2H, d, J=7.6 Hz), 6.47 (1H, s), 7.15 (1H, br s), 7.51 (1H, d, J=8.2 Hz), 7.80 (1H, d, J=8.2 Hz), 8.81 (1H, s).

Example 30

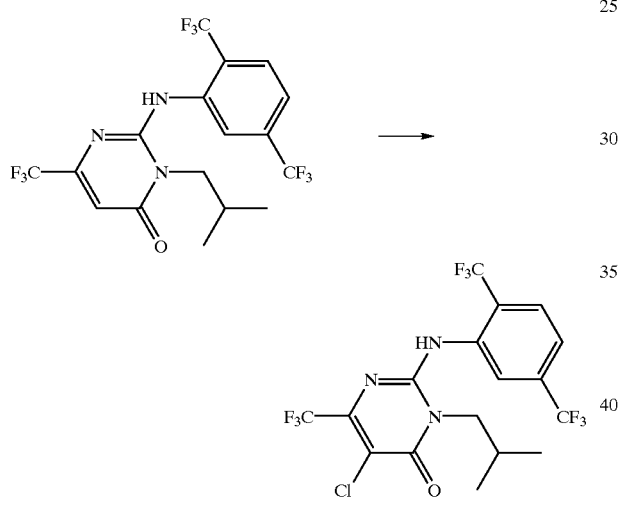

Sulfuryl chloride (0.16 ml) was added to acetic acid (14 ml) solution of 2-{2,5-bis(trifluoromethyl)phenyl}amino-3-isobutyl-6-trifluoromethyl-4(3H)-pyrimidinone (630 mg, 1.41 mmol), followed by stirring at room temperature for 3 hours. After completion of the reaction, ether (50 ml) and saturated sodium bicarbonate aqueous solution (50 ml) were added to the reaction solution to separate the organic layer, and the resulting aqueous layer was extracted with ether (30 ml×2). The thus obtained ether layers were combined, washed with sodium bicarbonate aqueous solution (50 ml) and saturated brine (50 ml) and dried over anhydrous sodium sulfate, and then the solvent was evaporated under a reduced pressure. By purifying the thus obtained crude product by a column chromatography (dichloromethane:hexane=7:3), white solid of 2-{2,5-bis (trifluoromethyl)phenyl}amino-5-chloro-3-isobutyl-6-trifluoromethyl-4(3H)-pyrimidinone [Compound No. 57] was obtained.

Yield: 96%; mp: 143–145° C.; $^1$H-NMR (CDCl$_3$, TMS, ppm): δ 1.08 (6H, d, J=6.7 Hz), 213–228 (1H, m), 4.01 (2H, d, J=7.4 Hz), 7.15 (1H, s), 7.55 (1H, d, J=8.2 Hz), 7.81 (1H, d, J=8.2 Hz), 8.84 (1H, s).

Example 31

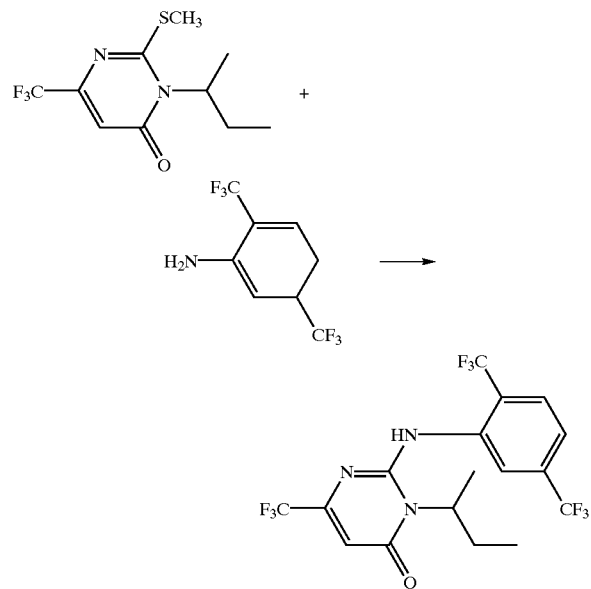

3-sec-Butyl-2-methylthio-6-trifluoromethyl-4(3H)-pyrimidinone which had been synthesized in accordance with the method of Example 24 was allowed to react with 2,5-bis(trifluoromethyl)aniline, thereby obtaining 2-{2,5-bis (trifluoromethyl)phenyl}amino-3-sec-butyl-6-trifluoromethyl-4(3H)-pyrimidinone [Compound No. 58] as a white solid.

Yield: 74.3%; mp: 165–167° C.; $^1$H-NMR, (CDCl$_3$, TMS, ppm): δ 1.00 (3H, t, J=7.4 Hz), 1.60 (3H, d, J=7.2 Hz), 2.00 (2H, m), 518–583 (1H, m), 6.44 (1H, s), 7.05 (1H, s), 7.54 (1H, d, J=8.2 Hz), 7.80 (1H, d, J=8.2 Hz), 8.52 (1H, s).

Example 32

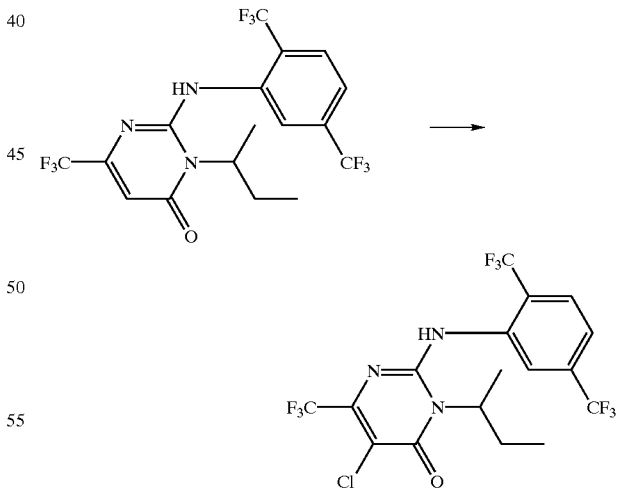

A dichloromethane (10 ml) solution of 2-{2,5-bis (trifluoromethyl)phenyl}amino-3-sec-butyl-6-trifluoromethyl-4(3H)-pyrimidinone (430 mg, 0.96 mmol) and N-chlorosuccinimide (141 mg, 1.06 mmol) was heated under reflux for 4 hours. After completion of the reaction, the solvent was evaporated under a reduced pressure, the resulting residue was suspended in ether (20 ml) and then the solid deposited was filtered. The resulting filtrate was washed with saturated sodium bicarbonate aqueous solution and saturated brine, dried over anhydrous magnesium sulfate, and then the solvent was evaporated under a reduced pressure. By purifying the thus obtained residue by a silica gel column chromatography (toluene), 2-{2,5-bis(trifluoromethyl)phenyl}amino-3-sec-butyl-5-chloro-6-trifluoromethyl-4(3H)-pyrimidinone [Compound No. 59] was obtained as colorless crystals.

Yield: 28%; mp: 133–135° C.; $^1$H-NMR (CDCl$_3$, TMS, ppm): δ 1.01 (3H, t, J=7.3 Hz), 1.63 (3H, d, J=7.2 Hz), 1.95–2.06 (2H, m), 4.93–5.78 (1H, m), 7.05 (1H, s), 7.56 (1H, d, J=8.5 Hz), 7.81 (1H, d, J=8.5 Hz), 8.55 (1H, s).

Example 33

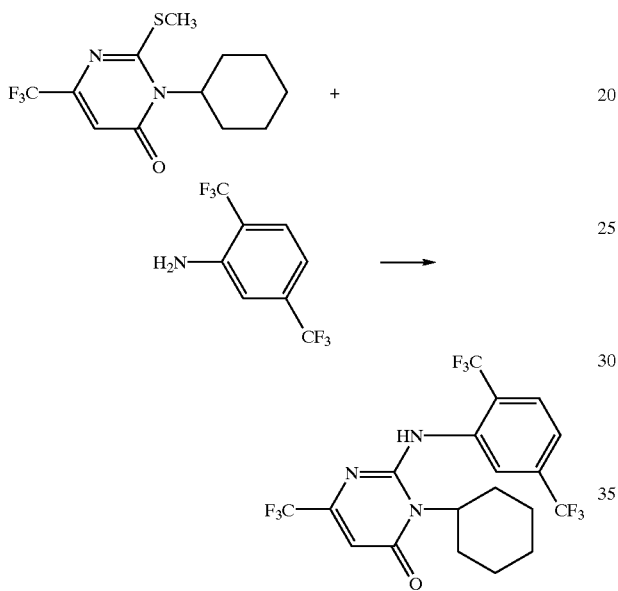

3-Cyclohexyl-2-methylthio-6-trifluoromethyl-4(3H)-pyrimidinone which had been synthesized in accordance with the method of Example 24 was allowed to react with 2,5-bis(trifluoromethyl)aniline, thereby obtaining white solid of 2-{2,5-bis(trifluoromethyl)phenyl}amino-3-cyclohexyl-6-trifluoromethyl-4(3H)-pyrimidinone [Compound No. 64].

Yield: 60%; mp: 154–156° C.; $^1$H-NMR (CDCl$_3$, TMS, ppm): δ 1.17–1.32 (2H, m), 1.43–1.60 (2H, m), 1.75–2.34 (7H, m), 4.60–5.80 (1H, m), 6.44 (1H, s), 7.22 (1H, s), 7.53 (1H, d, J=8.2 Hz), 7.80 (1H, d, J=8.2 Hz), 8.60 (1H, s).

Example 34

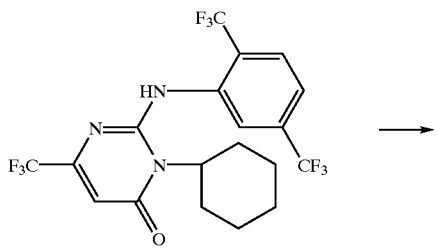

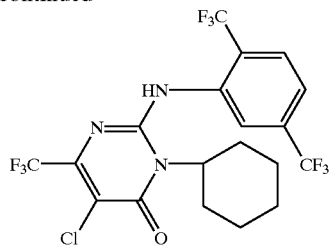

In accordance with the method of Example 25, chlorination of 2-{2,5-bis(trifluoromethyl)phenyl}amino-3-cyclohexyl-6-trifluoromethyl-4(3H)-pyrimidinone (80 mg, 0.18 mmol) was carried out using sulfuryl chloride to obtain white solid of 2-{2,5-bis(trifluoromethyl)phenyl}amino-5-chloro-3-cyclohexyl-6-trifluoromethyl-4(3H)-pyrimidinone [Compound No. 65].

Yield: 93%; mp: 181–183° C.; $^1$H-NMR (CDCl$_3$, TMS, ppm): δ 1.18–1.33 (1H, m), 1.42–1.59 (2H, m), 1.76–2.40 (7H, m), 4.45–5.55 (1H, m), 7.21 (1H, s), 7.54 (1H, d, J=8.2 Hz), 7.81 (1H, d, J=8.2 Hz), 8.64 (1H, s).

Example 35

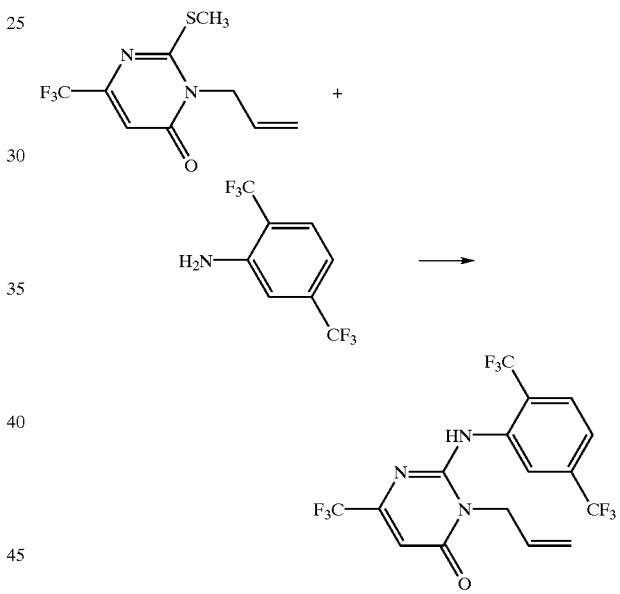

3-Allyl-2-methylthio-6-trifluoromethyl-4(3H)-pyrimidinone (1.14 g, 4.56 mmol) was dissolved in DMF (15 ml), and 2,5-bis(trifluoromethyl)aniline (0.55 ml, 3.52 mmol) was added. Sodium hydride (60% in oil, 0.23 g, 5.75 mmol) was added with stirring under ice-cooling, followed by stirring at room temperature for 1 hour and then at 70° C. for 2.5 hours. After completion of the reaction, ether (30 ml) and saturated ammonium chloride aqueous solution (30 ml) were added to the reaction solution to separate the organic layer, and the resulting aqueous layer was extracted with ether (20 ml×2). The organic layers were combined, washed with saturated brine (20 ml×2) and then dried over anhydrous sodium sulfate. The drying agent was removed by filtration, and the resulting filtrate was concentrated under a reduced pressure. By purifying the thus obtained crude product by a silica gel column chromatography (hexane), 3-allyl-2-{2,5-bis(trifluoromethyl)phenyl}amino-6-trifluoromethyl-4(3H)pyrimidinone [Compound No. 66] was obtained as a white solid.

Yield: 89%; mp: 116–118° C.; $^1$H-NMR (CDCl$_3$, TMS, ppm): δ 4.83 (2H, ddd, J=5.2, 1.7 and 1.7 Hz), 5.40 (1H, ddt, J =17.4, 1.7 and 1.7 Hz), 5.59 (1H, ddt, J=10.4, 1.7 and 1.7 Hz), 5.95 (1H, ddt, J=17.4, 10.4 and 5.2 Hz), 6.50 (1H, s), 7.17 (1H, s), 7.54 (1H, d, J=8.2 Hz), 7.78 (1H, d, J=8.2 Hz), 8.53 (1H, s).

Example 36

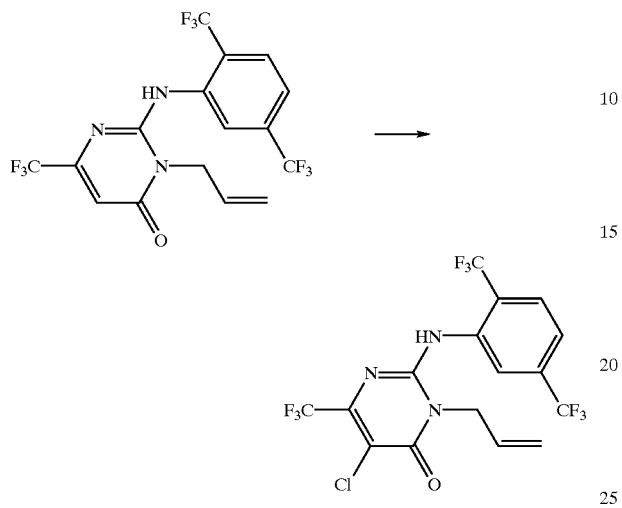

At room temperature, hexane solution of sulfuryl chloride (1.2 M, 0.56 ml, 0.67 mmol) was added to a mixture of 3-allyl-2-(2,5-bis(trifluoromethyl)phenyl)amino-6-trifluoromethyl-4-(3H)-pyrimidinone (0.29 g, 0.67 mmol) and acetic acid (6 ml), followed by stirring for 1 hour. After completion of the reaction, ether (30 ml) and saturated sodium bicarbonate aqueous solution (10 ml) were added to the reaction solution to separate the organic layer, and the resulting aqueous layer was extracted with ether (20 ml×2). The organic layers were combined, washed with saturated sodium bicarbonate aqueous solution and saturated brine in that order and then dried over anhydrous sodium sulfate. The drying agent was removed by filtration, and the solvent was evaporated under a reduced pressure from the resulting filtrate. By purifying the thus obtained crude product by a silica gel column chromatography (hexane:ethyl acetate= 3:1), 3-allyl-2-{2,5-bis(trifluoromethyl)phenyl}amino-5-chloro-6-trifluoromethyl-4(3H)-pyrimidinone [Compound No. 67] was obtained as a white solid.

Yield: 86.3%; mp: 149–152° C.; $^1$H-NMR (CDCl$_3$, TMS, ppm): δ 4.87 (2H, ddt, J=5.2, 1.7 and 1.7 Hz), 5.43 (1H, ddt, J=17.2, 1.7 and 1.7 Hz), 5.53 (1H, ddd, J=10.4, 1.7 and 1.7 Hz), 5.95 (1H, ddt, J=17.4, 10.4 and 5.2 Hz), 7.16 (1H, s), 7.56 (1H, d, J=8.2 Hz), 7.80 (1H, d, J=8.2 Hz), 8.58 (1H, s).

Example 37

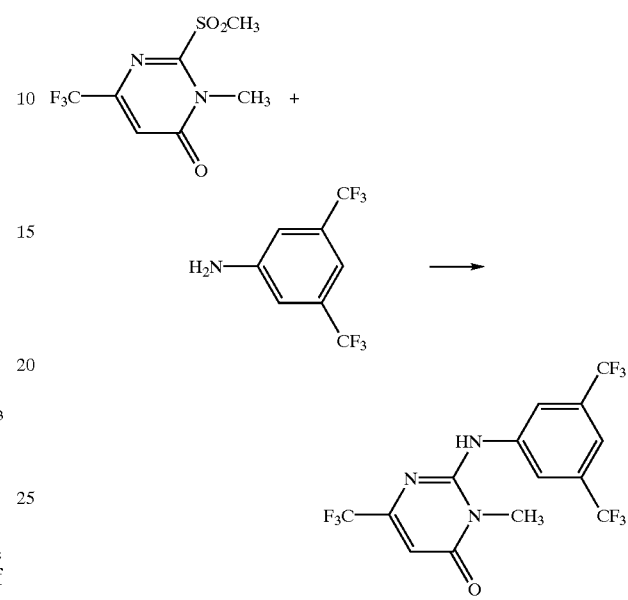

Reaction of 3,5-bis(trifluoromethyl)aniline with 3-methyl-2-methylsulfonyl-6-trifluoromethyl-4(3H)-pyrimidinone was carried out in accordance with the method of Example 7, thereby obtaining 2-{3,5-bis(trifluoromethyl) phenyl}amino-3-methyl-6-trifluoromethyl-4(3H)-pyrimidinone [Compound No. 67].

Yield: 13%; mp: 168.6–169.4° C.; $^1$H-NMR (CDCl$_3$, TMS, ppm): δ 3.65 (3H, s), 6.48 (1H, s), 6.9 (1H, br s), 7.69 (1H, s), 8.14 (2H, s).

Substituents are physical properties of the compounds of the present invention which can be produced by the methods exemplified in the above Examples are shown in Table 1, though this invention is not limited to these compounds unless overstepping its scope.

TABLE 1

2-Anilino-6-trifluoromethyl-4(3H)-pyrimidinone derivatives (I)

| No. | (R$^1$)m | R$^2$ | R$^3$ | X | Y | mp (° C.) |
|---|---|---|---|---|---|---|
| 1 | H | H | CH$_3$ | CF$_3$ | H | 193–184 |
| 2 | 3-Cl | H | CH$_3$ | CF$_3$ | H | 168.7–170.5 |
| 3 | 4-Cl | H | CH$_3$ | CF$_3$ | H | 237.1–238.8 |
| 4 | 2-F-4-Cl | H | CH$_3$ | CF$_3$ | H | 163–164 |

TABLE 1-continued

2-Anilino-6-trifluoromethyl-4(3H)-pyrimidinone derivatives (I)

| No. | (R¹)m | R² | R³ | X | Y | mp (° C.) |
|---|---|---|---|---|---|---|
| 5 | 2-F-4-Cl | $CH_3$ | $CH_3$ | $CF_3$ | H | viscous oil |
| 6(1) | 2,5-$Cl_2$ | H | $CH_3CH_2$ | $CF_3$ | H | 167–168 |
| 7(2) | 2,5-$Cl_2$ | H | $H_2C=CHCH_2$ | $CF_3$ | H | 118–120 |
| 8(3) | 2,4-$F_2$-3-Cl | H | $H_2C=CHCH_2$ | $CF_3$ | H | 86–88 |
| 9 | 2,4-$F_2$-3-Cl | H | $CH_3$ | $CF_3$ | H | 136–137 |
| 10 | 2,3,4-$Cl_3$ | H | $CH_3$ | $CF_3$ | H | 168–170 |
| 11 | 2,3,4-$Cl_3$ | $CH_3$ | $CH_3$ | $CF_3$ | H | 130–132 |
| 12 | 2,4,5-$Cl_3$ | H | $CH_3$ | $CF_3$ | H | 190.6–191.6 |
| 13 | 2,4,5-$Cl_3$ | H | $CH_3CH_2$ | $CF_3$ | H | 164–166 |
| 14 | 2,4,5-$Cl_3$ | H | $CH_3(CH_2)_3$ | $CF_3$ | H | 118–120 |
| 15(4) | 2,4,5-$Cl_3$ | H | $H_2C=CHCH_2$ | $CF_3$ | H | 145–147 |
| 16(5) | 2,3,4,5,6-$F_5$ | H | $CH_3CH_2$ | $CF_3$ | H | 146–149 |
| 17(6) | 2,3,4,5,6-$F_5$ | H | $CH_3CH_2$ | $CF_3$ | Cl | 180–182 |
| 18 | 2-Cl-4-$CF_3$ | H | $CH_3$ | $CF_3$ | H | 120.6–123.4 |
| 19 | 2-Cl-4-$CF_3$ | H | $CH_3(CH_2)_3$ | $CF_3$ | H | 98.3–99.8 |
| 20(7) | 2-Cl-5-$CF_3$ | H | $CH_3$ | $CF_3$ | H | 158–159 |
| 21(8) | 2-Cl-5-$CF_3$ | $CH_3$ | $CH_3$ | $CF_3$ | H | 118–119 |
| 22(9) | 2-Cl-5-$CF_3$ | H | $CH_3(CH_2)_3$ | $CF_3$ | H | 157–158 |
| 23(10) | 2-Cl-5-$CF_3$ | H | $(CH_3)_2CHCH_2$ | $CF_3$ | H | 118–119 |
| 24 | 2-Cl-5-$CF_3$ | H | $C_{12}H_{25}$ | $CF_3$ | H | viscous liquid |
| 25 | 3-$CF_3$-4-Cl | H | $CH_3$ | $CF_3$ | H | 239.5–240.3 |
| 26 | 2-$CH_3$S-3-Cl-4-F | H | $CH_3$ | $CF_3$ | H | 157–159 |
| 27 | 2-CN-3-Cl | H | $CH_3$ | $CF_3$ | H | 177.9–179.0 |
| 28(11) | 2,6-$Cl_2$-4-$CF_3$ | H | $CH_3$ | $CF_3$ | H | 212.5–213.2 |
| 29 | 2,6-$Cl_2$-4-$CF_3$ | H | $CH_3(CH_2)_3$ | $CF_3$ | H | 156.2–156.8 |
| 30(12) | 4-$(CH_3)_3$CH | H | $CH_3$ | $CF_3$ | H | amorphous solid |
| 31 | 3-$CF_3$ | H | $CH_3$ | $CF_3$ | H | 137.0–137.9 |
| 32 | 4-$CF_3$ | H | $CH_3$ | $CF_3$ | H | 222.1–223.6 |
| 33(13) | 2,4-$(CF_3)_2$ | H | $CH_3CH_2$ | $CF_3$ | H | 111.6–113.9 |
| 34(14) | 2,4-$(CF_3)_2$ | H | $CH_3CH_2$ | $CF_3$ | Cl | 124.1–124. |
| 35 | 2,4-$(CF_3)_2$ | $CH_3$ | $CH_3CH_2$ | $CF_3$ | H | viscous liquid |
| 36(15) | 2,4-$(CF_3)_2$ | $CH_3OCH_2$ | $CH_3CH_2$ | $CF_3$ | H | viscous liquid |
| 37(16) | 2,4-$(CF_3)_2$ | $CH_3CH_2OCH_2$ | $CH_3CH_2$ | $CF_3$ | H | 51–52 |
| 38(17) | 2,4-$(CF_3)_2$ | $CH_3CH_2OCH_2$ | $CH_3CH_2$ | $CF_3$ | Cl | viscous liquid |
| 39(18) | 2,4-$(CF_3)_2$ | $CH_3CO$ | $CH_3CH_2$ | $CF_3$ | H | 92–94 |
| 40(19) | 2,4-$(CF_3)_2$ | $CH_3OOC$ | $CH_3CH_2$ | $CF_3$ | H | viscous liquid |
| 41(20) | 2,4-$(CF_3)_2$ | $CH_3CH_2OOC$ | $CH_3CH_2$ | $CF_3$ | H | 48–50 |
| 42 | 2,4-$(CF_3)_2$ | $C_6H_5OOC$ | $CH_3CH_2$ | $CF_3$ | H | 107–109 |
| 43(21) | 2,4-$(CF_3)_2$ | $CH_3SO_2$ | $CH_3CH_2$ | $CF_3$ | H | viscous liquid |
| 44 | 2,4-$(CF_3)_2$ | H | $H_2C=CHCH_2$ | $CF_3$ | H | 80–82 |
| 45(22) | 2,4-$(CF_3)_2$ | $CH_3OCH_2$ | $H_2C=CHCH_2$ | $CF_3$ | H | viscous liquid |
| 46(23) | 2,5-$(CF_3)_2$ | H | $CH_3$ | $CF_3$ | H | 155–156 |
| 47(24) | 2,5-$(CF_3)_2$ | H | $CH_3CH_2$ | $CF_3$ | H | 173–175 |
| 48 | 2,5-$(CF_3)_2$ | $CH_3CH_2OCH_2$ | $CH_3CH_2$ | $CF_3$ | H | viscous liquid |
| 49(25) | 2,5-$(CF_3)_2$ | H | $CH_3CH_2$ | $CF_3$ | Cl | 144–146 |
| 50(26) | 2,5-$(CF_3)_2$ | H | $CH_3(CH_2)_2$ | $CF_3$ | H | 127–129 |
| 51(27) | 2,5-$(CF_3)_2$ | H | $CH_3(CH_2)_2$ | $CF_3$ | Cl | 124–126 |
| 52 | 2,5-$(CF_3)_2$ | H | $(CH_3)_2CH$ | $CF_3$ | H | 173–175 |
| 53 | 2,5-$(CF_3)_2$ | H | $(CH_3)_2CH$ | $CF_3$ | Cl | 153–155 |
| 54 | 2,5-$(CF_3)_2$ | H | $CH_3(CH_2)_3$ | $CF_3$ | H | 114–115 |
| 55(28) | 2,5-$(CF_3)_2$ | H | $CH_3(CH_2)_3$ | $CF_3$ | Cl | 121–122 |
| 56(29) | 2,5-$(CF_3)_2$ | H | $(CH_3)_2CHCH_2$ | $CF_3$ | H | 136–138 |
| 57(30) | 2,5-$(CF_3)_2$ | H | $(CH_3)_2CHCH_2$ | $CF_3$ | Cl | 143–145 |
| 58(31) | 2,5-$(CF_3)_2$ | H | $CH_3CH_2C(CH_3)H$ | $CF_3$ | H | 165–167 |
| 59(32) | 2,5-$(CF_3)_2$ | H | $CH_3CH_2C(CH_3)H$ | $CF_3$ | Cl | 133–135 |
| 60 | 2,5-$(CF_3)_2$ | H | $C_7H_{15}$ | $CF_3$ | H | 97–99 |
| 61 | 2,5-$(CF_3)_2$ | H | $C_8H_{17}$ | $CF_3$ | H | 80–82 |
| 62 | 2,5-$(CF_3)_2$ | H | $C_9H_{19}$ | $CF_3$ | H | 57–59 |
| 63 | 2,5-$(CF_3)_2$ | H | $C_{12}H_{25}$ | $CF_3$ | H | 35–38 |
| 64(33) | 2,5-$(CF_3)_2$ | H | cyclo-$C_6H_{11}$ | $CF_3$ | H | 154–156 |
| 65(34) | 2,5-$(CF_3)_2$ | H | cyclo-$C_6H_{11}$ | $CF_3$ | Cl | 181–183 |
| 66(35) | 2,5-$(CF_3)_2$ | H | $H_2C=CHCH_2$ | $CF_3$ | H | 116–118 |

TABLE 1-continued

2-Anilino-6-trifluoromethyl-4(3H)-pyrimidinone derivatives

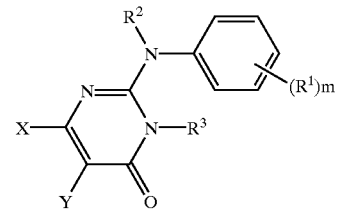

(I)

| No. | (R¹)m | R² | R³ | X | Y | mp (° C.) |
|---|---|---|---|---|---|---|
| 67(36) | 2,5-(CF₃)₂ | H | H₂C=CHCH₂ | CF₃ | Cl | 149–152 |
| 68 | 2,5-(CF₃)₂ | H | 2,3-dihydroxypropyl | CF₃ | H | 183–184 |
| 69(37) | 3,5-(CF₃)₂ | H | CH₃ | CF₃ | H | 168.6–169.4 |

Each number in ( ) indicates Example No.

The following shows formulation examples and test examples of the insecticidal and acaricidal agent of the present invention, though the invention is not limited to these examples. In this connection, the "No." of compound corresponds to respective compound No. of Examples. cl Formulation Example 1

Wettable Powder

To 20 parts by weight of the compound of the present invention were added 20 parts by weight of Carplex #80 (white carbon, Shionogi Pharmaceutical, trade name), 52 parts by weight of ST Kaolin Clay (kaolinite, Tsuchiya Kaolin, trade name), 5 parts by weight of Sorpol 9047K (anionic surfactant, Toho Chemical, trade name) and 3 parts by weight of Lunox P65L (anionic surfactant, Toho Chemical, trade name), and the mixture was uniformly mixed and pulverized to obtain a wettable powder containing 20% by weight of the active ingredient.

Formulation Example 2

Dust

To 2 parts by weight of the compound of the present invention were added 93 parts by weight of clay (manufactured by Nippon Talc) and 5 parts by weight of Carplex #80 (white carbon, Shionogi Pharmaceutical, trade name), and the mixture was uniformly mixed and pulverized to obtain a dust containing 2% by weight of the active ingredient.

Formulation Example 3

Emulsifiable Concentrate

In a mixed solvent composed of 35 parts by weight of xylene and 30 parts by weight of dimethylformamide was dissolved 20 parts by weight of the compound of the present invention, and the resulting solution was mixed with 15 parts by weight of Sorpol 3005X (mixture of a nonionic surfactant and an anionic surfactant, Toho Chemical, trade name) to obtain an emulsifiable concentrate containing 20% by weight of the active ingredient.

Formulation Example 4

Flowable

A mixture composed of 30 parts by weight of the compound of the present invention, 5 parts by weight of Sorpol 9047K (the same as the above), 3 parts by weight of Sorbon (nonionic surfactant, Toho Chemical, trade name), 8 parts by weight of ethylene glycol and 44 parts by weight of water was subjected to wet grinding using Daino Mill (manufactured by Shinmal Enterprises), and the resulting slurry-like mixture was mixed with 10 parts by weight of aqueous solution containing 1% by weight of xanthan gum (natural high polymer) and thoroughly pulverized to obtain a flowable containing 20% by weight of the active ingredient.

Test Example 1

Insecticidal Effect on Brown Rice Planthopper Larvae

A sprouted rice seedling was set in a glass cylinder (3 cm in inner diameter×17 cm in length), and 5 brown rice planthopper larvae of 4th instar were released therein. A water-diluted solution (0.5 ml) of the insecticide of the present invention (emulsifiable concentrate) produced in accordance with the method of Formulation Example 3 was applied to the just described glass cylinder (one concentration, two repetition) using a sprayer (manufactured by Mizuho Rika). After 5 days of the treatment, mortality and agony of the larvae were examined, and insecticidal ratio (%) was calculated by defining the larva in agony as ½ dead larvae. The results are shown in Table 2.

TABLE 2

Insecticidal effect on brown rice planthopper larvae

| Compound No. | Concentration (ppm) | Insecticidal ratio (%) |
|---|---|---|
| 46 | 500 | 100 |

Test Example 2

Insecticidal Effect on Diamondback Moth Larvae

A disc of cabbage leaf (6 cm in diameter) was cut out and soaked for 1 minute in a water-diluted solution of the insecticide of the present invention (wettable powder) produced in accordance with the method of Formulation Example 1. After the soaking, the disc was air-dried and set in a plastic cup (7 cm in inner diameter), and 5 diamondback moth larvae of 3rd instar were released therein (one concentration, two repetition). After 4 days of the release of larvae, mortality and agony of the larvae were examined, and insecticidal ratio (%) was calculated by defining the larvae in agony as ½ dead larvae. The results are shown in Table 3.

TABLE 3

Insecticidal effect on diamondback moth larvae

| Compound No. | Concentration (ppm) | Insecticidal ratio (%) |
|---|---|---|
| 20 | 500 | 100 |
| 46 | 500 | 100 |
| 56 | 500 | 100 |
| 69 | 500 | 100 |

Test Example 3

Acaricidal Effect on Two-Spotted Spider Mite Imagoes

A total of 10 two-spotted spider mite female imagoes were released on a disc cut out from a kidney bean leaf (3 cm in diameter). The acaricide of the present invention (wettable powder) produced in accordance with the method of Formulation Example 1 was diluted with water to a predetermined concentration, and the solution (3.5 ml) was applied on the just described cut leaf (one concentration, two repetition) using a rotary sprayer (manufactured by Mizuho Rika). After 24 hours of the treatment, mortality of the imagoes was examined to calculate acaricidal ratio (%). The results are shown in Table 4.

Test Example 4

Acaricidal Effect on Two-Spotted Spider Mite Eggs

A total of 5 two-spotted spider mite female imagoes were released on a disc cut out from a kidney bean leaf (3 cm in diameter). The thus released female imagoes were allowed to lay eggs on the cut leaf for 20 hours and then removed. The acaricide of the present invention (wettable powder) produced in accordance with the method of Formulation Example 1 was diluted with water to a predetermined concentration, and the solution (3.5 ml) was applied on the just described disc (one concentration, two repetition) using a rotary sprayer (manufactured by Mizuho Rika). After 8 days of the treatment, the number of unhatched eggs and the number of hatched imagoes were examined to calculate egg-killing ratio (%). The results are shown in Table 4.

TABLE 4

Acaricidal effect on imagoes and eggs of two-spotted spider mite

| Compound No. | Concentration (ppm) | Acaricidal ratio (%) imagoes | eggs |
|---|---|---|---|
| 22 | 500 | 100 | 100 |
| 46 | 500 | 100 | 100 |
| 56 | 500 | 100 | 100 |

Test Example 5

Insecticidal Effect on Common Cutworm Larvae

A disc of cabbage leaf (6 cm in diameter) was cut out and soaked for 1 minute in a water-diluted solution of the insecticide of the present invention (wettable powder) produced in accordance with the method of Formulation Example 1. After the soaking, the leaf disc was air-dried and set in a plastic cup (7 cm in inner diameter), and 5 common cutworm larvae of 3rd instar were released therein (one concentration, two repetition). The thus released larvae were kept in a constant temperature chamber at 25° C., mortality and agony of the larvae were examined 5 days thereafter, and insecticidal ratio (%) was calculated by defining the larva in agony as ½ dead larvae. The results are shown in Table 5.

TABLE 5

Insecticidal effect on common cutworm larvae

| Compound No. | Concentration (ppm) | Insecticidal ratio (%) |
|---|---|---|
| 20 | 500 | 100 |
| 23 | 500 | 100 |
| 46 | 500 | 100 |
| 56 | 500 | 100 |
| 69 | 500 | 100 |

Test Example 6

Insecticidal Effect on Adzuki Beam Weevil Imagoes

Two adzuki beans were set in a glass cylinder (3 cm in inner diameter×15 cm in length), and 10 adzuki bean weevil larvae were released therein. A water-diluted solution (0.3 ml) of the insecticide of the present invention (emulsifiable concentrate) produced in accordance with the method of Formulation Example 3 was applied to the just described glass cylinder (one concentration, two repetition) using a sprayer (manufactured by Mizuho Rika). These larvae were kept in a constant temperature chamber at 25° C., mortality and agony of the larvae were examined 4 days after the treatment, and insecticidal ratio (%) was calculated by defining the larva in agony as ½ dead larvae. The results are shown in Table 6.

TABLE 6

Insecticidal effect on adzuki bean weevil imagoes

| Compound No. | Concentration (ppm) | Insecticidal ratio (%) |
|---|---|---|
| 46 | 500 | 100 |
| 56 | 500 | 100 |

Test Example 7

Insecticidal Effect on Green Peach Aphid Larvae

A petiole part of a radish leaf was put into a screw bottle (capacity: 10 ml) filled with water, and 5 to 6 per one leaf of green peach aphid imagoes were inoculated. After the inoculation, the resulting bottle was put into a glass cylinder (3.5 cm in diameter and 15 cm in height, equipped with a mesh cover), and the green peach aphid imagoes were allowed to propagate in a constant temperature chamber at 25° C. for 3 days. After removal of the green peach aphid imagoes from the radish leaf, the resulting leaf was soaked (about 5 seconds) in a water-diluted solution of the insecticide (emulsifiable concentrate) of the present invention and then returned into the glass cylinder (one concentration, two repetition). The cylinder was kept in the constant temperature chamber of 25° C., and the number of aphid individuals on the radish leaf was examined on the 4th day after the treatment to calculate the insecticidal ratio (%) based on the result. The results are shown in Table 7.

TABLE 7

Insecticidal effect on green peach aphid larvae

| Compound No. | Concentration (ppm) | Insecticidal ratio (%) |
|---|---|---|
| 46 | 500 | 100 |

INDUSTRIAL APPLICABILITY

The insecticidal and acaricidal agent which contains, as the active ingredient, the anilinopyrimidinone derivative of the present invention shows markedly excellent preventive activity upon various insanitary insects or insect pests harmful to the agricultural and horticultural products, particularly upon insects and mites. The anilinopyrimidinone derivative of the present invention is useful as an active ingredient of insecticides and acaricides for agricultural and horticultural use.

What is claimed is:

1. An anilinopyrimidinone compound represented by general formula (II):

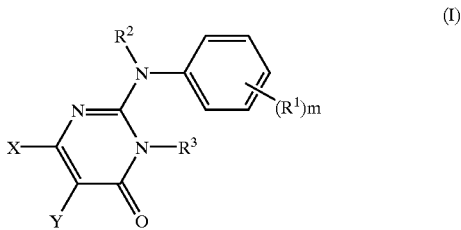

(II)

wherein
$R^{11}$ represents a chlorine atom or a trifluoromethyl group, n is 1 or 2, wherein $R^{11}$ may be the same or different from each other and at least one of $R^{11}$ is a trifluoromethyl group, $R^{21}$ represents a hydrogen atom, a $C_1$–$C_6$ alkyl group, a $C_2$–$C_6$ alkenyl group, a $C_3$–$C_6$ alkynyl group, a $C_1$–$C_6$ haloalkyl group, a ($C_1$–$C_4$ alkoxy) $C_1$–$C_4$ alkyl group, a $C_1$–$C_4$ alkoxy ($C_1$–$C_4$ alkoxy) $C_1$–$C_4$ alkyl group, a ($C_1$–$C_4$ haloalkoxy) $C_1$–$C_4$ alkyl group, a ($C_1$–$C_4$ alkylthio) $C_1$–$C_4$ alkyl group, a carboxy ($C_1$–$C_4$ alkyl) group, a ($C_1$–$C_4$ alkoxy) carbonyl ($C_1$–$C_4$ alkyl) group, a ($C_1$–$C_4$ alkoxy) carbonyloxy ($C_1$–$C_4$ alkyl) group, a ($C_1$–$C_5$ acyloxy) $C_1$–$C_4$ alkyl group, a cyano ($C_1$–$C_4$ alkyl) group, a cyanothio ($C_1$–$C_4$ alkyl) group, a $C_1$–$C_5$ acyl group, a ($C_1$–$C_4$ alkoxy)carbonyl group, an aminocarbonyl group, a ($C_1$–$C_6$ alkyl) aminocarbonyl group, a di($C_1$–$C_6$ alkyl)aminocarbonyl group, a ($C_1$–$C_6$ alkyl) sulfonyl group, a benzenesulfonyl group which may be substituted or a $C_7$–$C_8$ aralkyl group which may be substituted, $R^{31}$ represents a $C_1$–$C_6$ alkyl group, a $C_3$–$C_6$ alkenyl group or a $C_3$–$C_7$ cycloalkyl group, and $Y^1$ represents a hydrogen atom or a halogen atom, wherein two —$CF_3$ groups are present at either positions 2,4- or 2,5- on the phenyl ring.

2. The anilinopyrimidinone compound of claim 1, wherein:
$R^{11}$ is a trifluoromethyl group, and
$Y^1$ is a hydrogen atom or a chlorine atom.

3. The anilinopyrimidinone compound of claim 1, wherein:
$R^{11}$ is a trifluoromethyl group,
$R^{21}$ is selected from the group consisting of a hydrogen atom, a $C_1$–$C_6$ alkyl group, a ($C_1$–$C_4$ alkoxy) $C_1$–$C_4$ alkyl group, a ($C_1$–$C_4$ alkylthio) $C_1$–$C_4$ alkyl group, a ($C_1$–$C_5$ acyloxy) $C_1$–$C_4$ alkyl group, a ($C_1$–$C_4$ alkoxy) carbonyl group and a ($C_1$–$C_6$ alkyl) sulfonyl group, and
$Y^1$ is a hydrogen atom or a chlorine atom.

4. An anilinopyrimidinone compound represented by the following general formula (I):

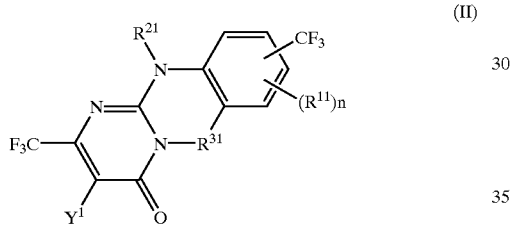

(I)

wherein:
$R^1$ is a halogen atom or a $C_1$–$C_4$ haloalkyl group, and m is an integer of from 2 to 5, with the proviso that at least two $R^1$ groups are $C_1$–$C_4$ haloalkyl groups, $R^2$ represents a hydrogen atom, a $C_1$–$C_6$ alkyl group, a $C_2$–$C_6$ alkenyl group, a $C_3$–$C_6$ alkynyl group, a $C_1$–$C_6$ haloalkyl group, a ($C_1$–$C_4$ alkoxy) $C_1$–$C_4$ alkyl group, a $C_1$–$C_4$ alkoxy ($C_1$–$C_4$ alkoxy) $C_1$–$C_4$ alkyl group, a ($C_1$–$C_4$ haloalkoxy) $C_1$–$C_4$ alkyl group, a ($C_1$–$C_4$ alkylthio) $C_1$–$C_4$ alkyl group, a carboxy ($C_1$–$C_4$ alkyl) group, a ($C_1$–$C_4$ alkoxy) carbonyl ($C_1$–$C_4$ alkyl) group, a ($C_1$–$C_4$ alkoxy) carbonyloxy($C_1$–$C_4$ alkyl) group, a ($C_1$–$C_5$ acyloxy) $C_1$–$C_4$ alkyl group, a cyano ($C_1$–$C_4$ alkyl) group, a cyanothio ($C_1$–$C_4$ alkyl) group, a $C_1$–$C_5$ acyl group, a ($C_1$–$C_4$ alkoxy)carbonyl group, an aminocarbonyl group, a ($C_1$–$C_6$ alkyl) aminocarbonyl group, a di ($C_1$–$C_6$ alkyl) aminocarbonyl group, a ($C_1$–$C_6$ alkyl) sulfonyl group, a benzenesulfonyl group which may be substituted or a $C_7$–$C_8$ aralkyl group which may be substituted, $R^3$ represents a hydrogen atom, a $C_1$–$C_6$ alkyl group, a $C_3$–$C_6$ alkenyl group, a $C_3$–$C_6$ alkynyl group, a $C_3$–$C_7$ cycloalkyl group or an amino group, X represents a halogen atom, a $C_1$–$C_4$ alkyl group or a $C_1$–$C_4$ haloalkyl group, and Y represents a hydrogen atom or a halogen atom, wherein two —$CF_3$ groups are present at either positions 2,4- or 2,5-on the phenyl ring.

5. The compound of claim 4, wherein X is $C_1$–$C_4$ haloalkyl group.

6. The compound of claim 4, wherein Y is hydrogen or chlorine.

7. The compound of claim 4, wherein $R^2$ is selected from the group consisting of hydrogen, a $C_1$–$C_6$ alkyl group, a ($C_1$–$C_4$ alkoxy) $C_1$–$C_4$ alkyl group, a ($C_1$–$C_4$ alkylthio) $C_1$–$C_4$ alkyl group, a ($C_1$–$C_5$) acyloxyl $C_1$–$C_4$ alkyl group, a ($C_1$–$C_4$ alkoxy)carbonyl group and a ($C_1$–$C_6$ alkyl) sulfonyl group.

8. The compound of claim 4, wherein $R^3$ is selected from the group consisting of a $C_1$–$C_6$ alkyl group, a $C_3$–$C_6$ alkenyl group and a $C_3$–$C_7$ cycloalkyl group.

9. A composition comprising the compound of claim 1 and an agricultural adjuvant or carrier.

10. A composition comprising the compound of claim 2 and an agricultural adjuvant or carrier.

11. A composition comprising the compound of claim 3 and an agricultural adjuvant or carrier.

12. A composition comprising the compound of claim 4 and an agricultural adjuvant or carrier.

13. A method for controlling an insect or acarid comprising contacting said insect or acarid with an effective amount of an insecticidal or acaricidal composition which comprises, as an active ingredient the compound of claim 1.

14. A method for controlling an insect or acarid comprising contacting said insect or acarid with an effective amount of an insecticidal or acaricidal composition which comprises, as an active ingredient the compound of claim 2.

15. A method for controlling an insect or acarid comprising contacting said insect or acarid with an effective amount of an insecticidal or acaricidal composition which comprises, as an active ingredient the compound of claim 3.

16. A method for controlling an insect or acarid comprising contacting said insect or acarid with an effective amount of an insecticidal or acaricidal composition which comprises, as an active ingredient the compound of claim 4.

17. A method for controlling an insect or acarid comprising contacting said insect or acarid with an effective amount of an insecticidal or acaricidal composition which comprises, as an active ingredient:

an anilinopyrimidinone compound represented by the following general formula (I):

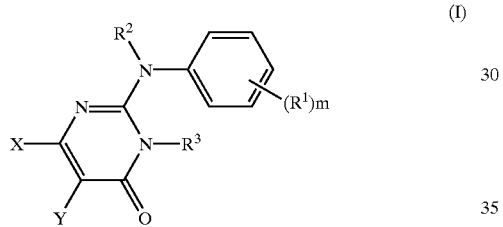

wherein $R^1$ represents a hydrogen atom, a halogen atom, a $C_1$–$C_4$ alkyl group, a $C_1$–$C_4$ alkoxy group, a ($C_1$–$C_4$ alkoxy) $C_1$–$C_4$ alkyl group, a $C_1$–$C_4$ haloalkyl group, a $C_1$–$C_4$ haloalkoxy group, a $C_1$–$C_4$ alkylthio group, a $C_1$–$C_4$ alkylsulfinyl group, a $C_1$–$C_4$ alkylsulfonyl group, a $C_1$–$C_5$ acyl group, a ($C_1$–$C_4$ alkoxy) carbonyl group, a $C_3$–$C_6$ alkenyl group, a $C_3$–$C_6$ alkenyloxy group, a $C_3$–$C_6$ alkynyl group, a $C_3$–$C_6$ alkynyloxy group, a $C_1$–$C_5$ acyloxy group, a ($C_1$–$C_4$ alkoxy) $C_1$–$C_4$ alkoxy group, a carboxy ($C_1$–$C_4$ alkyl) group, a ($C_1$–$C_4$ alkoxy) carbonyl ($C_1$–$C_4$ alkyl) group, a carboxy ($C_1$–$C_4$ alkoxy) group, a ($C_1$–$C_4$ alkoxy) carbonyl ($C_1$–$C_4$ alkoxy) group, a $C_1$–$C_4$ alkylamino group, a di ($C_1$–$C_4$ alkyl) amino group, a $C_1$–$C_5$ acylamino group, a $C_1$–$C_4$ alkylsulfonylamino group, a mercapto group, a cyano group, a carboxy group, an amino group or a hydroxyl group, m is an integer of from 1 to 5, with the proviso that $R^1$ may be the same or different from each other when m is an integer of from 2 to 5, $R^2$ represents a hydrogen atom, a $C_1$–$C_6$ alkyl group, a $C_2$–$C_6$ alkenyl group, a $C_3$–$C_6$ alkynyl group, a $C_1$–$C_6$ haloalkyl group, a ($C_1$–$C_4$ alkoxy) $C_1$–$C_4$ alkyl group, a $C_1$–$C_4$ alkoxy ($C_1$–$C_4$ alkoxy) $C_1$–$C_4$ alkyl group, a ($C_1$–$C_4$ haloalkoxy) $C_1$–$C_4$ alkyl group, a ($C_1$–$C_4$ alkylthio) $C_1$–$C_4$ alkyl group, a carboxy ($C_1$–$C_4$ alkyl) group, a ($C_1$–$C_4$ alkoxy) carbonyl ($C_1$–$C_4$ alkyl) group, a ($C_1$–$C_4$ alkoxy) carbonyloxy($C_1$–$C_4$ alkyl) group, a ($C_1$–$C_5$ acyloxy) $C_1$–$C_4$ alkyl group, a cyano ($C_1$–$C_4$ alkyl) group, a cyanothio ($C_1$–$C_4$ alkyl) group, a $C_1$–$C_5$ acyl group, a ($C_1$–$C_4$ alkoxy)carbonyl group, an aminocarbonyl group, a ($C_1$–$C_6$ alkyl) aminocarbonyl group, a di ($C_1$–$C_6$ alkyl) aminocarbonyl group, a ($C_1$–$C_6$ alkyl) sulfonyl group, a benzenesulfonyl group which may be substituted or a $C_7$–$C_8$ aralkyl group which may be substituted, $R^3$ represents a hydrogen atom, a $C_1$–$C_6$ alkyl group, a $C_3$–$C_6$ alkenyl group, a $C_3$–$C_6$ alkynyl group, a $C_3$–$C_7$ cycloalkyl group or an amino group, X represents a halogen atom, a $C_1$–$C_4$ alkyl group or a $C_1$–$C_4$ haloalkyl group, and Y represents a hydrogen atom or a halogen atom.

18. The method of claim 17, wherein said insecticidal or acaricidal composition comprises, as an active ingredient, an anilinopyrimidinone compound represented by the general formula (I) wherein $R^1$ is a halogen atom or a haloalkyl group, $R^2$ is selected from the group consisting of a hydrogen atom, an $C_1$–$C_6$ alkyl group, a ($C_1$–$C_4$ alkoxy) $C_1$–$C_4$ alkyl group, a ($C_1$–$C_4$ alkylthio) $C_1$–$C_4$ alkyl group, a ($C_1$–$C_5$ acyloxy) $C_1$–$C_4$ alkyl group, a ($C_1$–$C_4$ alkoxy) carbonyl group, and a ($C_1$–$C_6$ alkyl) sulfonyl group, $R^3$ is selected from the group consisting of a $C_1$–$C_6$ alkyl group, a $C_3$–$C_6$ alkenyl group, and a $C_3$–$C_7$ cycloalkyl group, X is a halogen atom or a $C_1$–$C_4$ haloalkyl group, Y is a hydrogen atom or a halogen atom and m is from 1 to 3.

* * * * *